US012380686B2

(12) United States Patent
Toporek et al.

(10) Patent No.: US 12,380,686 B2
(45) Date of Patent: Aug. 5, 2025

(54) ULTRASOUND IMAGING DATASET ACQUISITION FOR NEURAL NETWORK TRAINING AND ASSOCIATED DEVICES, SYSTEMS, AND METHODS

(71) Applicant: KONINKLIJKE PHILIPS N.V., Eindhoven (NL)

(72) Inventors: Grzegorz Andrzej Toporek, Boston, MA (US); Haibo Wang, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1266 days.

(21) Appl. No.: 16/979,613

(22) PCT Filed: Mar. 5, 2019

(86) PCT No.: PCT/EP2019/055357
§ 371 (c)(1),
(2) Date: Sep. 10, 2020

(87) PCT Pub. No.: WO2019/174953
PCT Pub. Date: Sep. 19, 2019

(65) Prior Publication Data
US 2021/0038321 A1    Feb. 11, 2021

Related U.S. Application Data

(60) Provisional application No. 62/641,493, filed on Mar. 12, 2018.

(51) Int. Cl.
*A61B 34/00*    (2016.01)
*A61B 8/00*    (2006.01)
(Continued)

(52) U.S. Cl.
CPC ............ *G06V 10/82* (2022.01); *A61B 8/0883* (2013.01); *A61B 8/12* (2013.01); *A61B 8/14* (2013.01);
(Continued)

(58) Field of Classification Search
CPC ..................................................... A61B 34/20
See application file for complete search history.

(56) References Cited

U.S. PATENT DOCUMENTS 4,894,013 A    1/1990  Smith et al.
5,181,514 A    1/1993  Solomon et al.
(Continued)

FOREIGN PATENT DOCUMENTS

WO    2015110882 A1    7/2015
WO    2015110943 A1    7/2015
WO    2017051279 A1    3/2017

OTHER PUBLICATIONS

Hahn et al: "Guidelines for Performing a Comprehensive Transesophageal Echocardiographic Examination:Recommendations From the American Society of Echocardiography and the Society of Cardiovascular Anesthesiologists"; American Society of Echocardiography, 2013, pp. 921-964.
(Continued)

*Primary Examiner* — Joseph M Santos Rodriguez

(57) ABSTRACT

Ultrasound image devices, systems, and methods are provided. A medical ultrasound image system, comprising an communication interface in communication with an imaging device and configured to receive a first image representative of a subject's body from the imaging device while the imaging device is positioned at a first imaging position with respect to the subject's body; and transmit a motion control configuration for repositioning the imaging device from the first imaging position to a second imaging position; a processor in communication with the communication inter-
(Continued)

face and configured to generate a database by associating the first image, the motion control configuration, and a score associated with the second imaging position and a target image view including a clinical property; and a storage device in communication with the processor and configured to store the database to facilitate training of a predictive network for aligning the imaging device to the target image view.

20 Claims, 21 Drawing Sheets

(51) Int. Cl.
 *A61B 8/08* (2006.01)
 *A61B 8/12* (2006.01)
 *A61B 8/14* (2006.01)
 *A61B 34/20* (2016.01)
 *A61B 34/30* (2016.01)
 *G06V 10/764* (2022.01)
 *G06V 10/82* (2022.01)
(52) U.S. Cl.
 CPC .............. *A61B 8/4218* (2013.01); *A61B 8/54* (2013.01); *A61B 34/20* (2016.02); *A61B 34/30* (2016.02); *G06V 10/764* (2022.01); *A61B 2034/2063* (2016.02); *A61B 2034/303* (2016.02)

(56) References Cited

U.S. PATENT DOCUMENTS

| | | | |
|---|---|---|---|
| 7,845,949 B2 | 12/2010 | Wilkins et al. | |
| 8,303,505 B2 * | 11/2012 | Webler | G06T 7/38 600/447 |
| 2010/0167251 A1 | 7/2010 | Boutchko et al. | |
| 2011/0181702 A1 * | 7/2011 | Hauger | G01B 9/02091 348/46 |
| 2016/0324585 A1 | 11/2016 | Noonan et al. | |
| 2017/0252002 A1 * | 9/2017 | Mine | A61B 8/4218 |
| 2017/0262982 A1 | 9/2017 | Pagoulatos et al. | |
| 2017/0360403 A1 * | 12/2017 | Rothberg | A61B 8/065 |
| 2018/0028142 A1 | 2/2018 | Bhatia et al. | |

OTHER PUBLICATIONS

PCT/EP2019/055357 WO & ISR, Jun. 14, 2019, 14 Page Document.
Levine et al: "Learning Hand-Eye Coordination for Robotic Grasping With Deep Learning and Large-Scale Data Collection"; ISER, 2012.

* cited by examiner

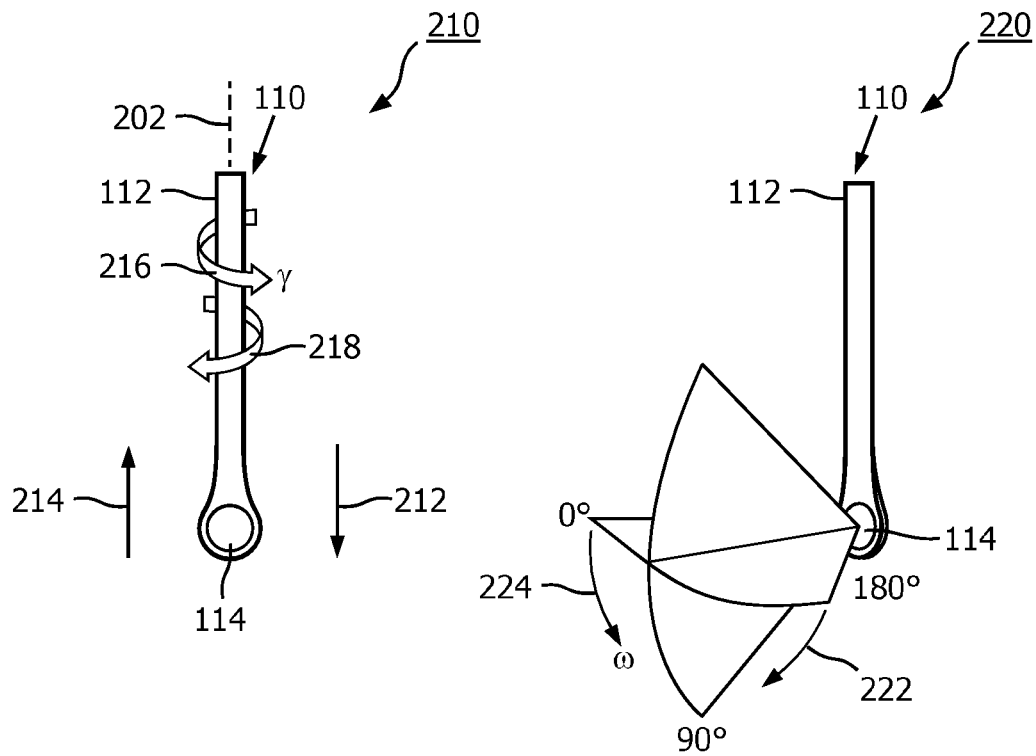
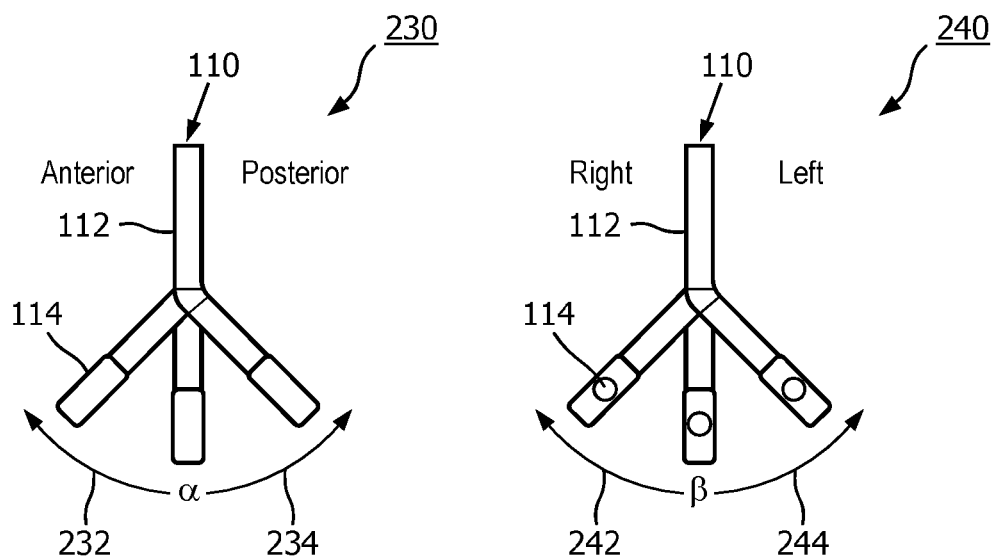
FIG. 2A  FIG. 2B
FIG. 2C  FIG. 2D

ULTRASOUND IMAGING DATASET ACQUISITION FOR NEURAL NETWORK TRAINING AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No PCT/EP2019/055357, filed on Mar. 5, 2019, which claims the benefit of U.S. Provisional Patent Application No. 62/641,493, filed on Mar. 12, 2018. These applications are hereby incorporated by reference herein.

RELATED APPLICATION

This application claims the benefit of and priority to U.S. Provisional Application No. 62/641,493, filed Mar. 12, 2018, which is incorporated by reference.

TECHNICAL FIELD

The present disclosure relates generally to ultrasound imaging, in particular, to acquiring large-scale ultrasound image datasets for training deep predictive networks to predict movements or controls for aligning imaging components to desired imaging planes.

BACKGROUND

Transesophageal echocardiography (TEE) uses ultrasound to capture images of a patient's heart movements and can be useful in clinical procedures. For example, a TEE probe may be inserted into a patient's esophagus for capturing images of the patient's heart. Some procedures that may benefit from TEE may include intraoperative procedures such as open heart and thoracic aortic surgery, guidance of transcatheter procedures such as transcatheter aortic valve implantation (TAVI), left atrial appendage closure (LAAC), and transcatheter mitral valve repair (TMVR), and diagnostic procedures. Alternatively, transthoracic echocardiography (TTE) is an external imaging technique that can be used to capture various views of a patient's heart from the outside of a patient's body. For example, a TTE probe may be placed on a patient's chest or abdomen for capturing images of the patient's heart.

In some instances, TEE may be more effective in capturing heart images than TTE. For example, a left atrial appendage (LAA) may not be visible from a TTE, but may be visible from a TEE. Recent studies have shown that LAA isolation may be a treatment option for patients with atrial fibrillation. LAA isolation can reduce the risk of embolic events. LAA isolation is typically performed percutaneously using a LAAC device. Prior to performing an LAA isolation procedure on a patient, a clinician may use a TEE probe to capture images of the patient's heart. The clinician may determine the size and/or the length of an LAA orifice in the patient's heart based on the images and may determine whether the size and/or the length of the LAA orifice are within the dimensions of the LAAC device. Given the complexity and anatomical variability of LAA, for example, the presence and the number of distinct lobes, a complete assessment of morphology typically requires imaging and delineation of the LAA from multiple views.

However, it may be challenging for a clinician to find an optimal view within a moving heart. For instance, a TEE probe may be advanced or withdrawn from a patient's esophagus, turned clockwise or counter-clockwise, flexed in four different directions, and the imaging plane can be rotated from 0 degrees to 180 degrees. Due to the multiple degrees of freedom, manual adjustments of a TEE probe can be cumbersome and time consuming.

SUMMARY

While existing procedures for using a TEE probe or a TTE probe have proved useful for clinical or therapy procedures, there remains a clinical need for improved systems and techniques for providing efficient, accurate, and automatic procedures for aligning an imaging component to a desired imaging plane. One approach to automating imaging component alignment without relying on similarity measures against reference images is to use statistical-based predictive networks. However, training of predictive networks typically requires a large amount of training data and the performance of the predictive networks may rely on the format and/or consistency of the training data. Collecting and constructing training datasets and/or validation datasets can be time consuming and expensive. Embodiments of the present disclosure provide mechanisms for acquiring large-scale ultrasound imaging datasets. The datasets can include annotations describing movements, controls, or positions of an imaging component (e.g., a TEE probe or a TTE probe) used for acquiring the images in the datasets. The datasets can include annotations describing whether the movements, controls, or positions of the imaging component can guide the imaging component to a target imaging plane for capturing a particular clinical property of a subject's body. The datasets associates images with corresponding annotations. The datasets can be acquired from a clinical setting or from a controlled setting using an anatomical phantom (e.g., a cardiac phantom). The datasets can be automatically acquired and annotated using a robotic system.

In one embodiment, a medical ultrasound image system is provided. The system includes a communication interface in communication with an imaging device and configured to receive a first image representative of a subject's body from the imaging device while the imaging device is positioned at a first imaging position with respect to the subject's body; and transmit a motion control configuration for repositioning the imaging device from the first imaging position to a second imaging position; a processor in communication with the communication interface and configured to generate a database by associating the first image, the motion control configuration, and a score representative of a relationship between the second imaging position and the first image with respect to a target image view including a clinical property; and a storage device in communication with the processor and configured to store the database to facilitate training of a predictive network for aligning the imaging device to the target image view.

In some embodiments, the motion control configuration includes one or more parameters for repositioning the imaging device to the second imaging position. In some embodiments, the processor is further configured to determine the one or more parameters. In some embodiments, the processor is further configured to determine the one or more parameters based on a random function. In some embodiments, the one or more parameters correspond to one or more of a movement of the imaging device along a left-right plane of the subject's body, a movement of the imaging device along an anterior-posterior plane of the subject's body, an orientation of an imaging plane of the imaging device, or a rotation of the imaging device with respect to an axis of the imaging device. In some embodiments, the imaging device is a transesophageal echocardiography (TEE) probe. In some embodiments, the one or more parameters correspond to at least one of a linear velocity or an angular velocity for moving the imaging device. In some embodiments, the imaging device is a transthoracic echocardiography (TTE) probe. In some embodiments, the communication interface is further configured to receive a second image representative of the subject's body while the imaging device is positioned at the second imaging position, and wherein the processor is further configured to determine the score based on a comparison between the second image and the target image view. In some embodiments, the processor is further configured to determine the score based on a comparison between the second imaging position and a target imaging position of the imaging device for obtaining an image of the subject's body corresponding to the target image view. In some embodiments, the score indicates a success when the second imaging position corresponds to a target imaging position of the imaging device for obtaining an image of the subject's body corresponding to the target image view. In some embodiments, the processor is further configured to determine the motion control configuration, and wherein the communication interface is further configured to transmit the motion control configuration to a robotic system controlling the imaging device.

In one embodiment, a method of medical ultrasound image data acquisition, comprising receiving, from an imaging device, a first image representative of a subject's body while the imaging device is positioned at a first imaging position with respect to the subject's body; transmitting a motion control configuration for repositioning the imaging device from the first imaging position to a second imaging position; and generating a database by associating the first image, the motion control configuration, and a score representative of a relationship between the second imaging position and the first image with respect to a target image view including a clinical property.

In some embodiments, the motion control configuration includes one or more parameters for moving the imaging device to the second imaging position. In some embodiments, the method further comprises determining the one or more parameters. In some embodiments, the imaging device is a transesophageal echocardiography (TEE) probe, and wherein the one or more parameters correspond to one or more of a movement of the imaging device along a left-right plane of the subject's body, a movement of the imaging device along an anterior-posterior plane of the subject's body, an orientation of an imaging plane of the imaging device, or a rotation of the imaging device with respect to an axis of the imaging device. In some embodiments, the imaging device is a transthoracic echocardiography (TTE) probe, and wherein the one or more parameters correspond to at least one of a linear velocity or an angular velocity for moving the imaging device. In some embodiments, the method further comprises receiving, from the imaging device, a second image representative of the subject's body while the imaging device is positioned at the second imaging position; and determining the score based on a comparison between the second image and the target image view. In some embodiments, the method further comprises determining the score based on a comparison between the second imaging position and a target imaging position of the imaging device for obtaining an image of the subject's body corresponding to the target image view. In some embodiments, the transmitting the motion control configuration includes transmitting the motion control configuration to a robotic system controlling the imaging device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2A is a schematic diagram illustrating a configuration for a TEE probe, according to aspects of the present disclosure.

FIG. 2B is a schematic diagram illustrating a configuration for a TEE probe, according to aspects of the present disclosure.

FIG. 2C is a schematic diagram illustrating a configuration for a TEE probe, according to aspects of the present disclosure.

FIG. 2D is a schematic diagram illustrating a configuration for a TEE probe, according to aspects of the present disclosure.

DETAILED DESCRIPTION

Figure 1:
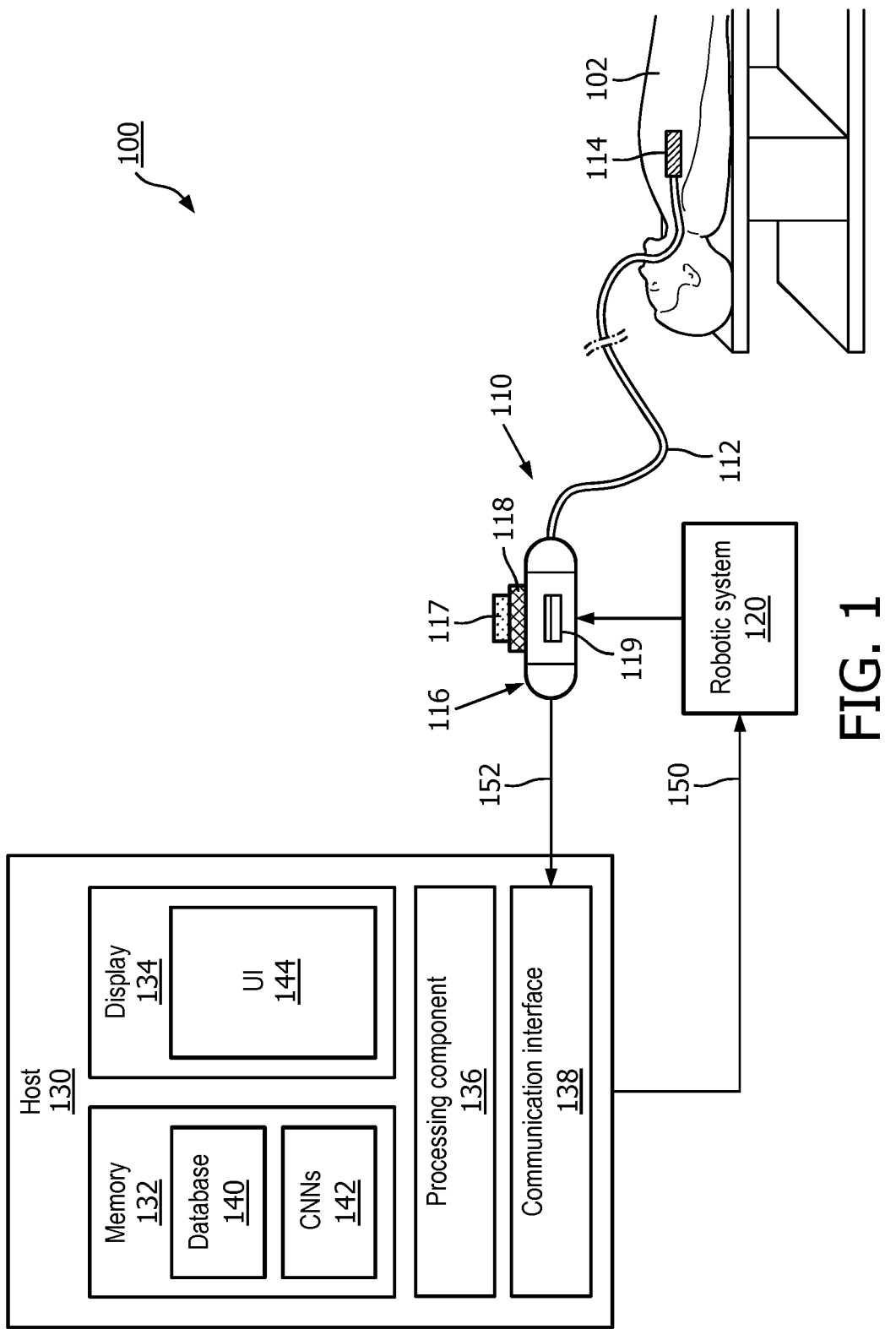
FIG. 1 is a schematic diagram of a medical imaging system including a transesophageal echocardiography (TEE) probe, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of a medical imaging system 100 including a TEE probe 110, according to aspects of the present disclosure. The system 100 includes a host 130, a robotic system 120, and the TEE probe 110 in communication with each other. At a high level, the TEE probe 110 can be inserted through a mouth of a patient 102 into an esophagus to capture images of a heart of the patient 102 and the host 130 can instruct the robotic system 120 to reposition the TEE probe 110 to a desired location. For instance, for an LAAC procedure, the host 130 may instruct the robotic system 120 to position the TEE probe 110 such that an image including an LAA of the heart may be captured by the TEE probe 110. The system 100 can be an ultrasound imaging system, and the probe 110 can be an ultrasound probe.

The TEE probe 110 may include a flexible elongate member 112, an imaging component 114, and a handle 116. The flexible elongate member 112 can be sized and/or shaped, structurally arranged, and/or otherwise configured to be positioned within a body lumen of a patient, such as an esophagus. The member 112 may be referred to as an endoscope. The imaging component 114 may be mounted at a distal end of the member 112. In some instances, the probe 110 can be a guide wire, a catheter, or a guide catheter. The imaging component 114 may include one or more ultrasound sensors or transducer elements. The imaging component 114 is configured to emit ultrasonic energy towards an anatomy (e.g., the heart) of the patient 102. The ultrasonic energy is reflected by the patient's vasculatures and/or tissue structures. The ultrasound transducer elements in the imaging component 114 may receive the reflected ultrasound echo signals. In some embodiments, the TEE probe 110 may include an internal or integrated processing component that can process the ultrasound echo signals locally to generate image signals representative of the patient 102's anatomy under imaging. The ultrasound transducer element(s) can be arranged to provide two-dimensional (2D) images or three-dimensional (3D) images of the patient 102's anatomy. The images acquired by the TEE probe 110 may be dependent on the depth of insertion, the rotation, and/or the tilt of the TEE probe 110, as described in greater detail herein.

The handle 116 may be coupled a proximal end of the member 112. The handle 116 may include control elements for maneuvering the imaging component 114 and/or the member 112. As shown, the handle 116 includes knobs 117 and 118 and a switch 119. The knob 117 may flex the member 112 and the imaging component 114 along an anterior-posterior plane of the patient 102 (e.g., heart). The knob 118 may flex the member 112 and the imaging component 114 along a left-right plane of the patient 102. The switch 119 may control beamforming at the imaging component 114 (e.g., adjusting an angle of an imaging plane).

The robotic system 120 may include electrical and/or mechanical components, such as motors, rollers, and gears, configured to control the handle 116 (e.g., dialing the knobs 117 and 118 and/or turning the switch 119 on and/or off). Alternatively, the robotic system 120 may be configured to manipulate the TEE probe 110 directly. The robotic system 120 may receive motion control commands from the host 130 and controls the knobs 117 and 118 and/or the switch 119 on the handle 116 and/or directly drive the TEE probe 110 based on the motion control commands. The motion control commands are described in greater detail herein.

The host 130 may include a memory 132, a display 134, a processing component 136, and a communication interface 138. The processing component 136 may be coupled to and in communication with the memory 132, the display 134, and the communication interface 138. The host 130 may be a computer work station, a mobile phone, a tablet, or any suitable computing device.

The memory 132 may be any suitable data storage device, such as a cache memory (e.g., a cache memory of the processing component 136), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 132 may be configured to store a database 140 and one or more CNNs 142.

The processing component 136 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 136 may also be implemented as a combination of computing devices, e.g., a combination of a DSP and a microprocessor, a plurality of microprocessors, one or more microprocessors in conjunction with a DSP core, or any other such configuration.

In an embodiment, the processing component 136 is configured to acquire images from a patient such as the patient 102 or an anatomical phantom (e.g., a cardiac phantom), generate motion control parameters for controlling the TEE probe 110, determine labels or scores for qualifying or validating the acquired images and the motion control parameters with respect to a target image view including a particular or selected clinical property, and/or generate the database 140. The database 140 may store the acquired images in association with the motion control parameters and the scores.

In an embodiment, the processing component 136 is configured to train the CNNs 142 for aligning the imaging component 114 to target image planes based on the database 140. In an embodiment, the processing component 136 is configured to apply the CNNs 142 in a clinical setting to determine motion control commands for the robotic system 120 to align the imaging component 114 to a patient such as the patient 102 for a clinical procedure. For instance, the imaging component 114 is aligned to obtain an image of an LAA of the patient 102 for a LAAC procedure. Mechanisms for acquiring the datasets for the database 140, training the CNNs 142, and applying the CNNs 142 are described in greater detail herein.

In some embodiments, the memory 132 may include a non-transitory computer-readable medium. The memory 132 may store instructions that, when executed by the processing component 136, cause the processing component 136 to perform the operations described herein with references to the data acquisition, CNN training, and/or CNN application in connection with embodiments of the present disclosure. Instructions may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer readable The display 134 may include a computer screen or any suitable display for displaying a user interface (UI) 144. The UI 144 may include a graphical representation or view of the handle 116, for example, including the knobs 117 and 118 and the switch 119. The UI 144 may include visual indicators indicating a direction and/or an amount to dial the knobs 117 and 118, an instruction to turn the switch 119 on or off, and/or a direction and/or a degree to rotate the TEE probe 110, as described in greater detail herein. While the display 134 is shown as an integrated component of the host 130, in some embodiments, the display 134 may be external to the host 130 and in communication with the host 130 via the communication interface 138. For instance, the display 134 may include a standalone display, an augmented reality glasses, or a mobile phone.

The communication interface 138 may include one or more processors, transmitters, one or more receivers, one or more transceivers, and/or circuitry for transmitting and/or receiving communication signals. The communication interface 138 can include hardware components and/or software components implementing a particular communication protocol suitable for transporting signals over the communication links 150 and 152. The communication interface 138 can be referred to as a communication device or a communication interface module. The communication interface 138 is configured to interface and communicate with the robotic system 120 and the imaging component 114 via communication links 150 and 152, respectively. For example, the host 130 may send motion control commands to the robotic system 120 over the communication link 150 and receive acquired images from the imaging component 114 via the communication link 152. The communication links 150 and 152 may include a wireless link and/or a wired link. Examples of a wireless link may include a low-power Bluetooth® wireless link, an Institute of Electrical and Electronics Engineers (IEEE) 802.11 (WiFi) link, or any suitable wireless link. Examples of a wired link may include a universal serial bus (USB) link or any suitable wired link.

In some embodiments, the UI 144 may display instructions for operating the handle 116 to align the TEE probe 110 to a desired location. For example, the processing component 136 may output the motion control commands in the format of instructions and/or visual indicators to the display 134 via the UI 144 and a clinician may manually align the TEE probe 110 to the patient 102 based on the instructions instead of employing the robotic system 120. The communication interface 138 may be further configured to receive user inputs, for example, via a keyboard, a mouse, or a touchscreen. The UI 144 may update a certain display or view based on the user input. The UI 144 is described in greater detail herein.

While the system 100 is illustrated with a TEE probe 110, the system 100 may be configured to automatically align any suitable imaging component to a patient for a clinical procedure. The imaging component may provide an internal imaging modality, where the imaging component may be inserted into a patient's body for obtaining an image of the patient's anatomy. Alternatively, the imaging component may provide an external imaging modality, where the imaging component may be placed external to a patient's body for obtaining an image of the patient's anatomy. Imaging modalities may include intravascular ultrasound (IVUS) imaging, forward looking intravascular ultrasound (FL-IVUS) imaging, intravascular photoacoustic (IVPA) imaging, intracardiac echocardiography (ICE), optical imaging, optical coherence tomography (OCT), radiographic imaging, x-ray imaging, angiography, fluoroscopy, computed tomography (CT), magnetic resonance imaging (MRI), elastography, etc.

In some other embodiments, the system 100 may include any suitable sensing component, including a pressure sensor, a flow sensor, a temperature sensor, an optical fiber, a reflector, a mirror, a prism, an ablation element, a radio frequency (RF) electrode, a conductor, and/or combinations thereof for performing a clinical or therapy procedure, where images of a patient's anatomy receiving the procedure may be captured by the imaging component 114 before, during, and/or after the procedure.

The TEE probe 110 may be maneuvered in various degrees of freedom. FIGS. 2A-D illustrate various mechanisms for maneuvering the TEE probe 110. FIG. 2A is a schematic diagram illustrating a configuration 210 for the TEE probe 110, according to aspects of the present disclosure. The TEE probe 110 can be manually advanced into a patient's esophagus as shown by the arrow 212 or withdrawn from the patient's esophagus as shown by the arrow 214. The TEE probe 110 can be manually rotated left (e.g., counter-clockwise) or right (e.g., clockwise) with respect to a longitudinal axis 202 of the TEE probe 110 as shown by the arrows 216 and 218, respectively. The rotations of the member 112 can be described by a parameter, denoted as γ.

FIG. 2B is a schematic diagram illustrating a configuration 220 for the TEE probe 110, according to aspects of the present disclosure. The TEE probe 110 can be electronically rotated from 0 degree to 180 degrees (e.g., for beamforming) as shown by the arrows 222 and 224, for example, by controlling the switch 119 on the handle 116. The rotations of the imaging planes can be described by a parameter, denoted as ω.

FIG. 2C is a schematic diagram illustrating a configuration 230 for the TEE probe 110, according to aspects of the present disclosure. The TEE probe 110 can be flexed along an anterior-posterior plane, for example, with respect to a patient's heart, as shown by the arrows 232 and 234, for example, by dialing the knob 118 on the handle 116. The flexing along the anterior-posterior plane can be described by a parameter, denoted as α.

FIG. 2D is a schematic diagram illustrating a configuration 240 for the TEE probe 110, according to aspects of the present disclosure. The TEE probe 110 can be flexed along a left-right plane, for example, with respect to a patient's heart, as shown by the arrows 242 and 244, for example, by dialing the knob 117 on the handle 116. The flexing along the left-right plane can be described by a parameter, denoted as β.

Figure 3:
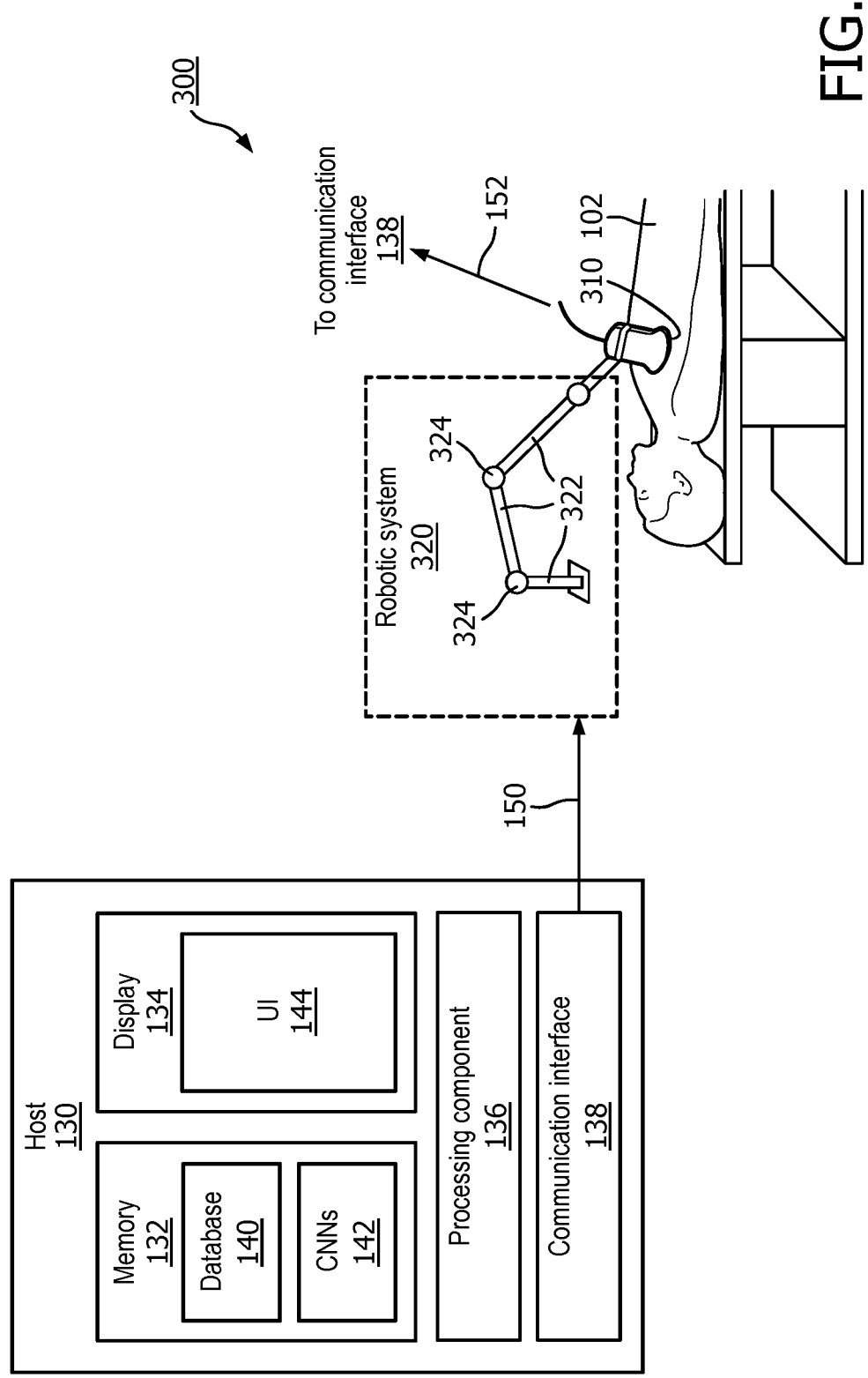
FIG. 3 is a schematic diagram of a medical imaging system including a transthoracic echocardiography (TTE) probe, according to aspects of the present disclosure.

FIG. 3 is a schematic diagram of a medical imaging system 300 including a TTE probe 310, according to aspects of the present disclosure. The system 300 is substantially similar to the system 100, but the system 300 is used to align an external imaging component (e.g., the TTE probe 310) to a target imaging plane instead of an internal imaging component (e.g., the TEE probe 110). As shown, the system 300 includes the host 130, a robotic system 320, and the TTE probe 310 in communication with each other. At a high level, the TTE probe 310 is configured to capture images of a patient 102's anatomy from the outside of the patient 102's body and the host 130 can instruct the robotic system 320 via the link 150 to reposition the TTE probe 310 to a desired location. The system 300 can be an ultrasound imaging system, and the probe 310 can be an ultrasound probe.

The TTE probe 310 may include an imaging component operating in substantially similar mechanisms as the imaging component 114. For example, imaging component may include ultrasound transducer elements arranged to capture 2D images or 3D images of the patient 102's anatomy (e.g., the heart) from external imaging. Similarly, the TTE probe 310 may send the acquired image signals to the host 130 via the link 152.

The robotic system 320 may include a plurality of links 322 coupled to a plurality of joints 324 configured to hold the TTE probe 310 and maneuver the TTE probe 310 on an external surface of the patient 102 (e.g., around the chest area for imaging the heart). The processing component 136 may generate the database 140 and the CNNs 142 using substantially similar mechanisms as in the system 100, but the motion control commands may be in the formats of Cartesian velocity instead of the rotating and flexing of the TEE probe 110, as described in greater detail herein.

Generally, the system 100, the system 300, the probe 110, the probe 310, and/or other devices described herein can be utilized to examine any suitable anatomy and/or lumen of the patient body 102. In some instances, the probe 110 can be positioned within the anatomy and/or lumen of the patient body 102. In other instances, the probe 110 can be positioned outside of body 102 to examine the anatomy and/or lumen inside of the body 102. For the anatomy and/or lumen may represent fluid filled or surrounded structures, both natural and man-made. For example, a probe of the present disclosure can be positioned within and/or used to examine an esophagus of the patient. In some embodiments, a probe of the present disclosure may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. The anatomy and/or lumen inside of the body 102 may be a blood vessel, as an artery or a vein of a patient's vascular system, including cardiac vasculature, peripheral vasculature, neural vasculature, renal vasculature, and/or or any other suitable lumen inside the body. In addition to natural structures, a probe of the present disclosure may be used to examine man-made structures such as, but without limitation, heart valves, stents, shunts, filters and other devices.

Figure 4:
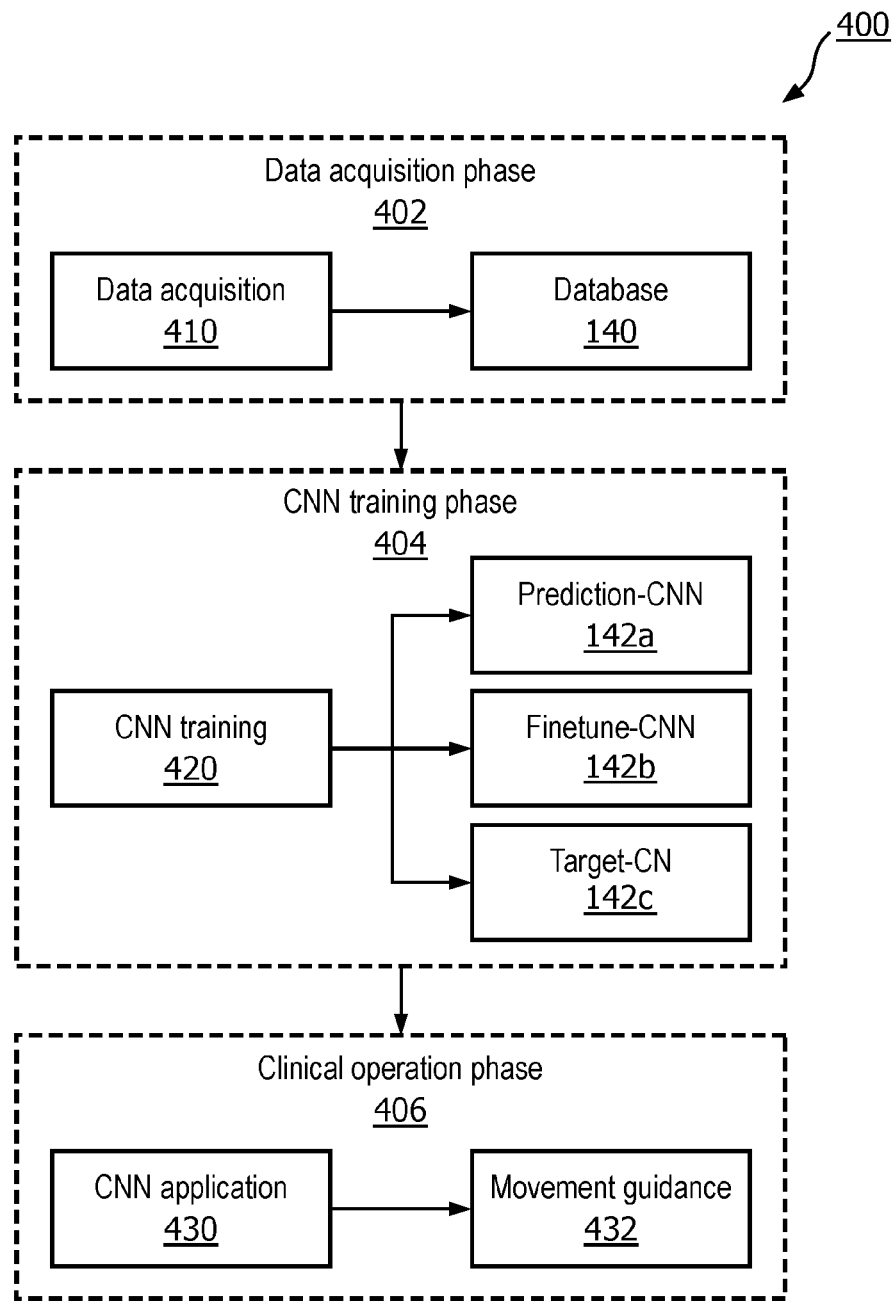
FIG. 4 is a schematic diagram illustrating a scheme for automating an imaging component alignment procedure, according to aspects of the present disclosure.

FIG. 4 is a schematic diagram illustrating a scheme 400 for automating an imaging component alignment procedure, according to aspects of the present disclosure. The scheme 400 may be implemented by the host 130 in the systems 100 and 300. The scheme 400 may include a data acquisition phase 402, a CNN training phase 404, and a clinical operational phase 406. The data acquisition phase 402 and the CNN training phase 404 may be performed offline and the clinical operational phase 406 may be performed in a clinical setting.

In the data acquisition phase 402, the data acquisition component 410 may be configured to acquire image data using an imaging component (e.g., the TEE probe 110 or the TTE probe 310), generate motion control parameters for maneuvering the imaging component (e.g., using the robotic system 120 or 320) to various locations with respect to a subject's body (e.g., the patient 102 or an anatomical phantom), and associate the locations of the imaging component and corresponding images with a target image view to generate the database 140. The data acquisition component 410 may automatically annotate or label the acquired images based on a relationship between corresponding positions of the imaging component and the target view. The data acquisition component 410 may acquire the data and update the database 140 iteratively or periodically. Mechanisms for acquiring the data and generating the database 140 are described in greater detail herein.

In the CNN training phase 404, the CNN training component 420 may be configured to train the CNNs 142 based on the database 140. The CNNs 142 may include a predictive-CNN 142a, a finetune-CNN 142b, and a target-CNN 142c. The predictive-CNN 142a is trained to receive a currently acquired image from the imaging component and infer or deduce a motion vector (e.g., including motion control parameters) with a highest probability of the imaging component reaching a desired location for capturing a target image view. For example, the predictive-CNN 142a may be trained for a target image view including a particular or predetermined clinical property (e.g., an LAA). The finetune-CNN 142b is trained to verify whether a pair of images have the same quality level or select an image having a higher quality level from the pair. The target-CNN 142c is trained to determine whether a target image view (e.g., an LAA) has been captured. In some embodiments, the CNN training component 420 may train the finetune-CNN 142b and/or the target-CNN 142c using additional clinical data. Mechanisms for training the CNNs 142 are described in greater detail herein.

In the clinical operational phase 406, the CNN application component 430 may apply the trained CNNs 142 to determine a motion vector for repositioning or aligning the imaging component to a patient's anatomy for obtaining a target image view. The CNN application component 430 may employ a closed loop control algorithm to for the alignment. For example, the CNN application component 430 may apply the prediction-CNN 142a to direct the imaging component and apply the target-CNN 142c to check whether the imaging component is at a desired location. The CNN application component 430 may repeatedly apply the predictive-CNN 142a and the target-CNN 142c until the target-CNN 142c detected the target image view. Subsequently, the CNN application component 430 may apply the finetune-CNN 142b to direct the imaging component to an optimal location for capturing the target image view. The CNN application component 430 may instruct the robotic system to reposition or align the imaging component in the alignment process. Alternatively, the CNN application component 430 may provide the motion vectors to the movement guidance component 432, for example, for display in the UI 144. Mechanisms for applying the CNNs 142 are described in greater detail herein.

Figure 5:
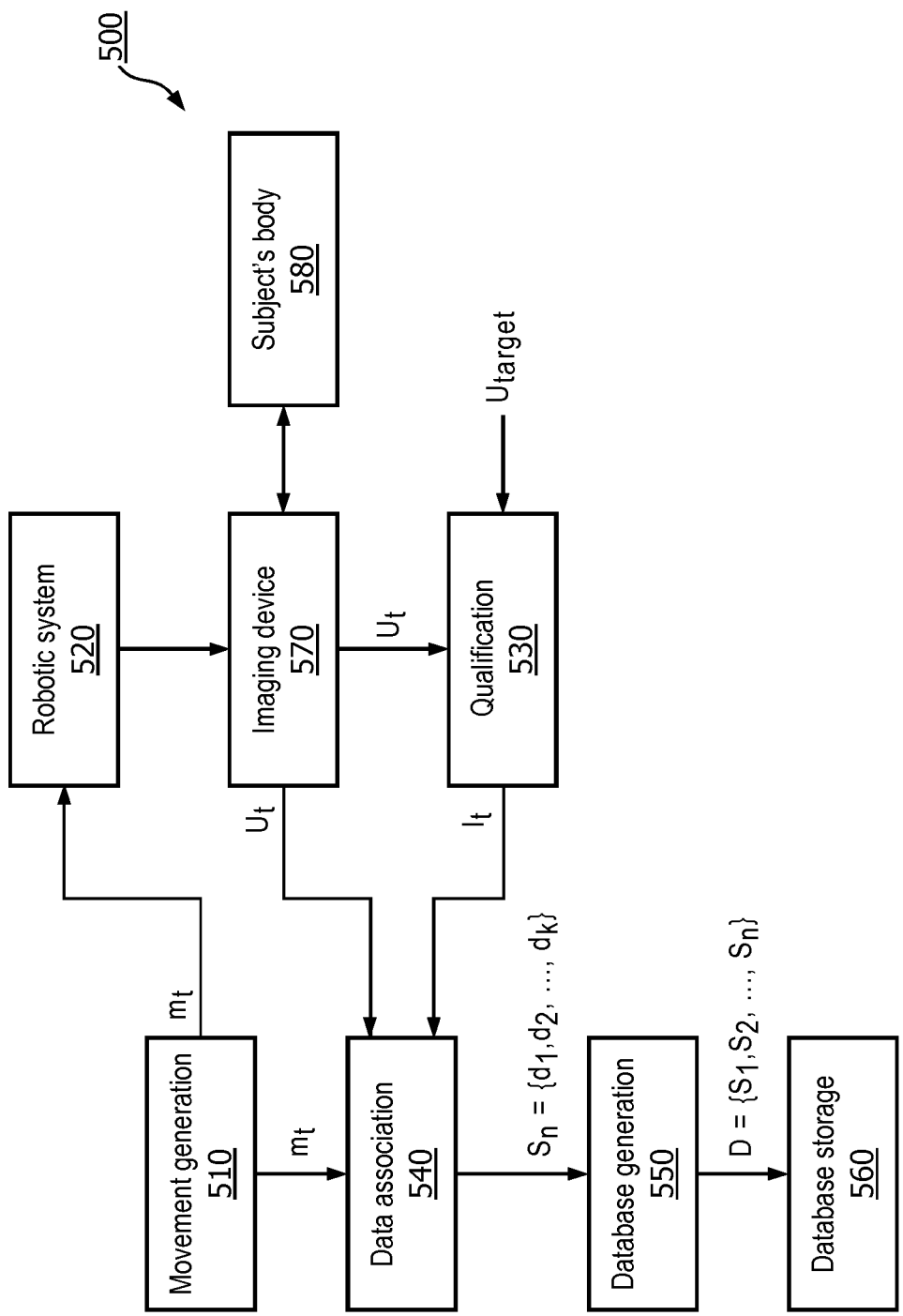
FIG. 5 is a schematic diagram illustrating a scheme for acquiring large-scale image datasets, according to aspects of the present disclosure.

FIG. 5 is a schematic diagram illustrating a scheme 500 for acquiring large-scale image datasets, according to aspects of the present disclosure. The scheme 500 may be implemented by the systems 100 and 300 and the data acquisition component 410. The scheme 500 provides a more detailed view of the automatic data acquisition process in the data acquisition phase 402. The scheme 500 includes a movement generation component 510, a robotic system 520, a qualification component 530, a data association component 540, a database generation component 550, a database storage component 560, and an imaging device 570. In an embodiment, the imaging device 570 may correspond to the TEE probe 110 and the robotic system 520 may correspond to the robotic system 120. In another embodiment, the imaging device 570 may correspond to the TTE probe 310 and the robotic system 520 may correspond to the robotic system 330.

The movement generation component 510 is configured to generate a set of imaging plane positions (e.g., for 2D imaging) and encode the imaging plane positions into motion control configurations. The motion control configurations are used to reposition the imaging device 570. The motion control configurations may be represented by motion vectors, denoted as $m_t$. The motion control configurations may include parameters that may vary depending on the type of imaging component in use. For example, when the imaging device 570 is a TEE probe 110, the motion control configurations may include parameters, $\gamma$, $\omega$, $\alpha$, and $\beta$, as shown and described with respect to FIGS. 2A, 2B, 2C, and 2D, respectively. Alternatively, when the imaging device 570 is a TTE probe 310, the motion control configurations may be represented by linear velocity parameters and angular velocity parameters. In some embodiments, the movement generation component 510 may employ a random function to generate parameters for the motion control configurations. The movement generation component 510 may provide the motion control configurations to the robotic system 520 and the data association component 540.

In some embodiments, the motion control configurations can include controls for operating the imaging device 570 to change an imaging plane within a volumetric ultrasound image in addition to changing a physical location of the imaging device 570. For example, an imaging plane may be tilted in an elevation direction or any suitable angle with respect to an axis of a volumetric region under volumetric imaging.

In general, the motion control configurations can include any measurable data related to a particular position or a particular motion of a device provided by a user or a robot. Various motion control configurations are described throughout the application, and methods/systems herein can involve any one or combination of these motion control configurations. In some instances, motion control configurations include one or more parameters. The parameters may include directional or velocity vectors and/or imaging plane positions.

The robotic system 520 may reposition the imaging device 570 based on the motion control configurations. The imaging device 570 may capture images of a subject's body 580 (e.g., a cardiac phantom) and provide the images, denoted as $U_t$, to the qualification component 530 and the data association component 540.

The qualification component 530 determines whether an acquired image includes a particular clinical property (e.g., an LAA) meaningful for a particular clinical procedure (e.g., an LAAC procedure). As an example, the scheme 500 may be configured to generate the database 140 for capturing a target image view, denoted as $U_{target}$, including a particular clinical property. The qualification component 530 may output a score or label, denoted as $l_t$. For example, when a selected motion control configuration positioned the imaging device 570 at a location where the acquired image is successful in capturing the target image view, the qualification component 530 may output a value of 1 for the score $l_t$. Conversely, when an acquired image fails to capture the target image view, the qualification component 530 may output a value of 0 for the score $l_t$. The qualification component 530 may provide the score $l_t$ to the data association component 540.

In an embodiment, the data association component 540 may receive a current image, denoted as $U_t$, captured by the imaging device 570 at a current position, denoted as $q_t$. The robotic system 520 may reposition the imaging device 570 to a next position, denoted as $q_{end}$, based on a motion control vector $m_t$, which may be represented as shown below:

$$m_t = q_{end} - q_t. \tag{1}$$

The qualification component 530 may receive a next image, denoted as $U_{t+1}$, of the subject's body 580 captured by the imaging device 570 when the imaging device 570 is repositioned to the position $q_{end}$. The qualification component 530 may determine the score $l_t$ for the motion command that resulted in generating the image $U_{t+1}$ based on whether the image $U_{t+1}$ includes the target image view $U_{target}$. Alternatively, when the subject's body 580 is a phantom, the target position for capturing the target image view is known. Thus, the qualification component 530 may determine the score $l_t$ by comparing the position $q_{end}$ to the target position.

The data association component 540 may associate the current image $U_t$ with the motion control vector $m_t$ and the score $l_t$ to form a data-tuple, denoted as $d_t$, as shown below:

$$d_t = (U_t, m_t, l_t). \tag{2}$$

The scheme 500 may take a sequence of K steps in each try or attempt in reaching the target image view, where K is a positive integer. Each try or attempt may be represented by a sequence, denoted as $S_n$, as shown below:

$$S_n = \{d_1, d_2, \ldots, d_K\}, \tag{3}$$

where $d_t$ may represent a data-tuple at a particular step t in the sequence $S_n$. The data association component 540 may provide the sequence $S_n$ to the database generation component 550.

A sequence $S_n$ may terminate under various conditions. For example, a sequence $S_n$ may terminate when a similarity measure between the image $U_{t+1}$ and the target image view $U_{target}$ is large. Various mechanisms may be used to determine a similarity measure between two unimodal images. For example, normalized cross-correlation, sum of squared difference (SSD), template matching, and/or siamese convolutional neural networks may be used to determine the similarity measure. Alternatively, a sequence $S_n$ may terminate when a position $q_{end}$ for a step $d_t$ corresponds to a known target location (e.g., a target coordinate registered with respect to the phantom). A sequence $S_n$ may also terminate when a number of tries or steps (e.g., K) exceeded a threshold without reaching the target image view or after exhausting all motion control parameters, for example, reaching a hardware limit for a particular motion or a software limit. An example of a hardware limit may be sweeping α, β, or γ for the flexing and rotating of the TEE probe 110 respectively. An example of a software limit may be sweeping ω for changing imaging planes through all angles from 0 to 180 degrees. In some instances, software limits may be arbitrarily defined by the robotic system 120 for each degree of freedom α, β, γ or ω.

The database generation component 550 may generate the database 140 by forming an associative dataset, denoted as D, from sequences $S_n$ obtained from N attempts as shown below:

$$D=\{S_1, S_2, \ldots, S_N\}, \qquad (4)$$

where N is a positive integer.

The database storage component 560 may store the database 140 or the dataset D in a memory such as the memory 132. In some embodiments, the scheme 500 may be performed using a phantom and then repeated using a clinical setting (e.g., capturing images of a patient 102). In such embodiments, the repositioning of the imaging device 570 may be performed manually by a user or automatically by the robotic system 520. When the repositioning of the imaging device 570 is performed manually, the movements may be sensed by a movement sensing component, which may record a motion control configuration based on the sensed movements. In addition, image/position qualification may be performed automatically by the qualification component 530 or manually by the user. In some instances, the UI 144 may include various settings for the user to qualify an acquired image or an image plane position or to indicate a final step in a sequence $S_n$.

In an embodiment, ultrasound imaging parameters, such as gain and depth, may be adjusted for the acquisition. In an embodiment, a clinician or user may select a target image view $U_{target}$ for a particular clinical procedure from a set of clinically relevant views recommended by a clinical community. In an embodiment, a clinician may manually locate a target image view $U_{target}$ based on an extensive search over an image volume. In another embodiment, a clinician may obtain several target image views with varying imaging parameters or positions for the acquisition.

In an embodiment, after the scheme 500 has generated a sufficient number of motion control configurations to acquire image datasets for a portion of an imaging volume, a clinician may reposition the imaging device 570 to a different location and repeat the scheme 500 to acquire a different portion of the imaging volume. In an embodiment, the scheme 500 may be repeated by using several other subject's body 580 (e.g., multiple cardiac phantoms) to increase the diversity of the acquired imaging datasets. In an embodiment, the scheme 500 may be repeated by using several imaging devices 570 (e.g., multiple TEE probes 110 or multiple TTE probes 310) to increase the diversity of the imaging datasets. The number of imaging plane positions or motion control configurations and the number of repetitions may be arbitrarily selected by a clinician. To support deep learning neural network training, the size of the imaging datasets is required to be relatively large.

While the scheme 500 is illustrated for generating a database 140 for a particular target view, the scheme 500 may be repeated for a different target image view. The scheme 500 may store datasets of different target image views in the same database or different databases.

Figure 6:
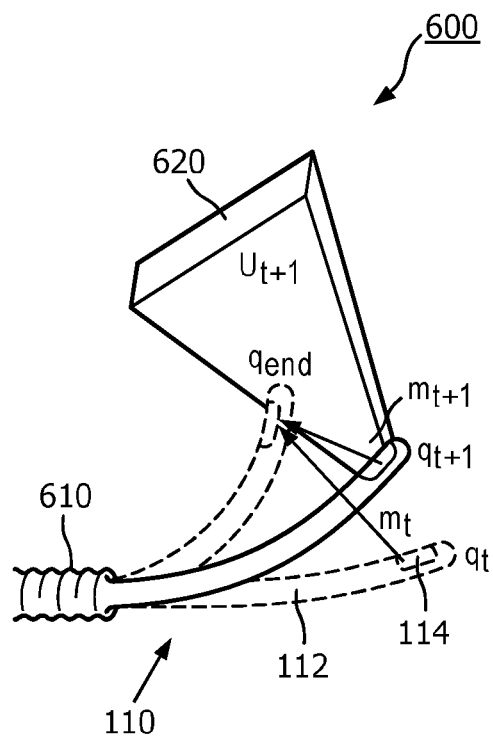
FIG. 6 is a schematic diagram illustrating a scenario for repositioning a TEE probe, according to aspects of the present disclosure.

FIG. 6 is a schematic diagram illustrating a scenario 600 for repositioning a TEE probe, according to aspects of the present disclosure. The scenario 600 may correspond to the step of repositioning the imaging device 570 when the imaging device 570 corresponds to the TEE probe 110. As shown, the TEE probe 110 may include an adjustable member 610 that flexes or adjusts the positioning of the member 112 and the imaging component 114. The imaging component 114 is moved along a sequence of positions, for example, from a current position $q_t$ to a next position $q_{t+1}$ and terminating at a terminating position $q_{end}$. When the TEE probe 110 is at the position $q_{t+1}$, the imaging component 114 may capture an image 620 (e.g., $U_{t+t}$). The motion control vector $m_t$ can be expressed as shown below:

$$m_t = q_{t+1} - q_t = (\alpha, \beta, \gamma, \omega)^T, \qquad (5)$$

where T represents a transpose operator.

Figure 7:
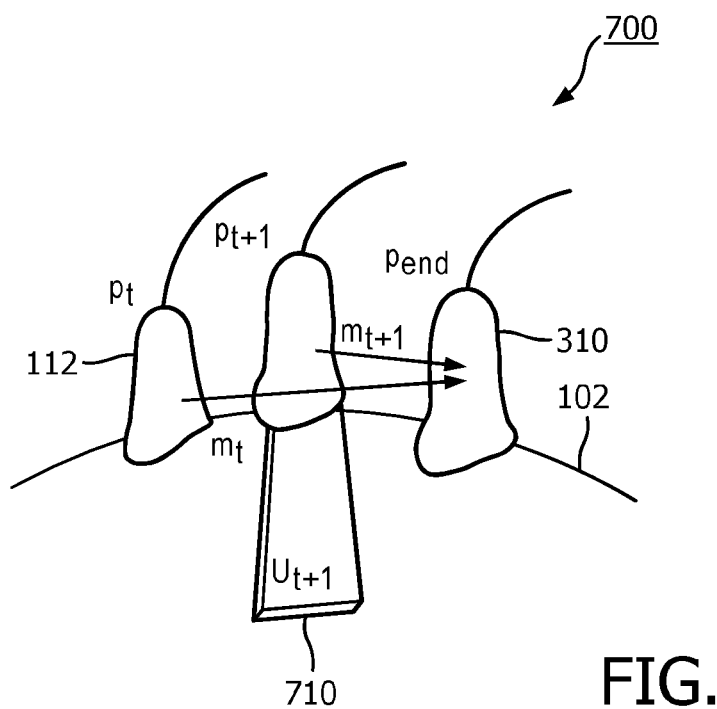
FIG. 7 is a schematic diagram illustrating a scenario for repositioning a TTE probe, according to aspects of the present disclosure.

FIG. 7 is a schematic diagram illustrating a scenario 700 for repositioning a TTE probe, according to aspects of the present disclosure. The scenario 700 may correspond to the step of repositioning the imaging device 570 when the imaging device 570 corresponds to the TTE probe 310. As shown, the TTE probe 310 may is moved along a sequence of positions, for example, from a current position represented by $p_t$ to a next position represented by $p_{t+1}$ and terminating at a terminating position represented by $p_{end}$, where $p_t$, $p_{t+1}$, and $p_{end}$ are 4-by-4 transformation matrices (e.g., including translations and rotations). Thus, the motion control vector $m_t$ can be represented by a 3D translation vector (e.g., linear velocity) and a change in orientation (e.g., angular velocity) around each axis (e.g., in an x-y-z space) from the current position to the end position. When the TTE probe 310 is at the position $p_{t+1}$, the TTE probe 310 may capture an image 710 (e.g., $U_{t+1}$) of the patient 102. The motion control vector $m_t$ can be expressed as shown below:

$$m_t = p_{t+1} - p_t = (v_{xt}, v_{yt}, v_{zt}, \omega_{xt}, \omega_{yt}, \omega_{zt})^T, \qquad (6)$$

where $v_{xt}$, $v_{yt}$, and $v_{zt}$ represent the linear velocities along the x, y, and z axes, respectively, and $\omega_{xt}$, $\omega_{yt}$, and $\omega_{zt}$ represent the angular velocities with respect to the x, y, and z axes, respectively. When applying the scheme 500 with a TTE probe 310, a user may arbitrarily determine a boundary condition or a terminating condition to limit the positions that the TEE probe 310 may be repositioned to (e.g., a boundary around a chest area of a patient when imaging the patient's heart).

Figure 8A:
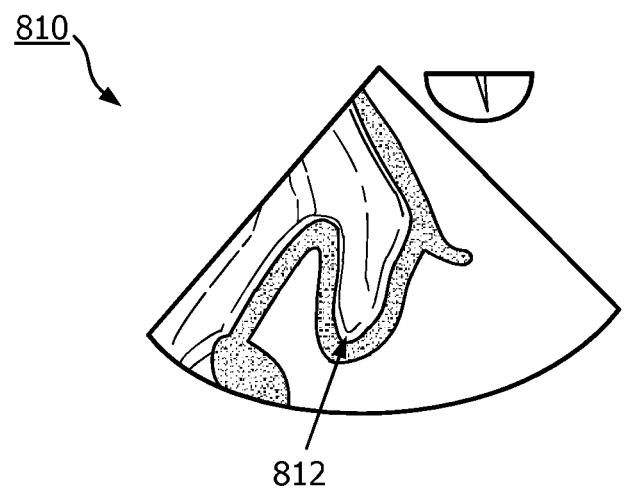
FIG. 8A illustrates an example of a target image view of an LAA, according to aspects of the present disclosure.
Figure 8B:
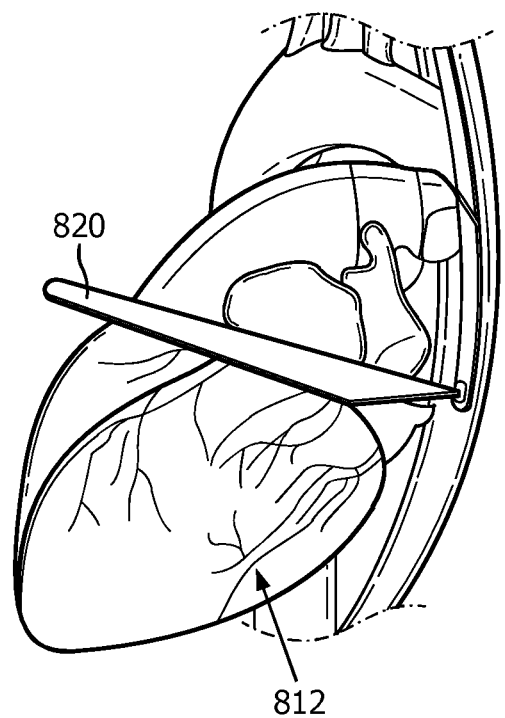
FIG. 8B illustrates an example of a position of an imaging plane for capturing an LAA, according to aspects of the present disclosure.
Figure 8C:
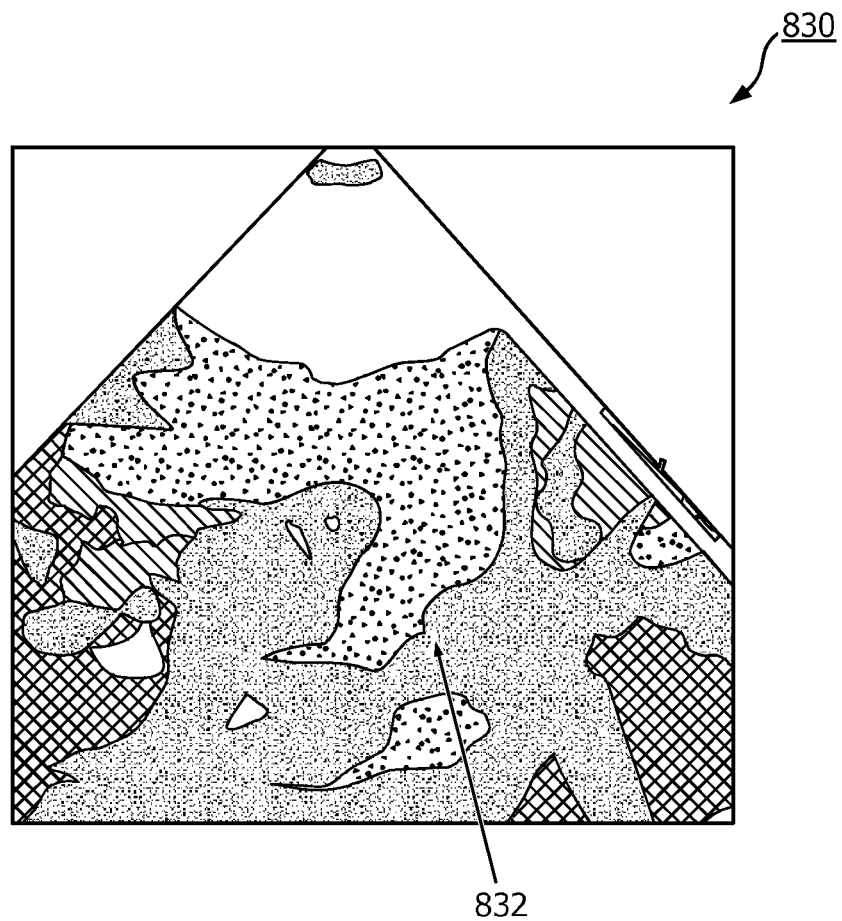
FIG. 8C illustrates an example of an image of an LAA captured by an imaging component, according to aspects of the present disclosure.

FIGS. 8A-8C illustrate various example images or image views that may correspond to the images used in the scheme 500. FIG. 8A illustrates an example of a target image view 810 of an LAA 812, according to aspects of the present disclosure. For example, the target image view 810 may correspond to $U_{target}$ and the LAA 812 may correspond to a desired clinical property. FIG. 8B illustrates an example of a position of an imaging plane 820 for capturing an LAA within a patient's heart 822, according to aspects of the present disclosure. For example, the scheme 500 may be used to reposition the imaging device 570 to capture an image with the imaging plane 820. FIG. 8C illustrates an example of a target image 830 of an LAA 832 captured by an imaging component at the image plane 820, such as the imaging device 570 or the TEE probe 110, according to aspects of the present disclosure. For example, the target image 830 may correspond to $U_{target}$ and the LAA 832 may correspond to a desired clinical property.

Figure 9:
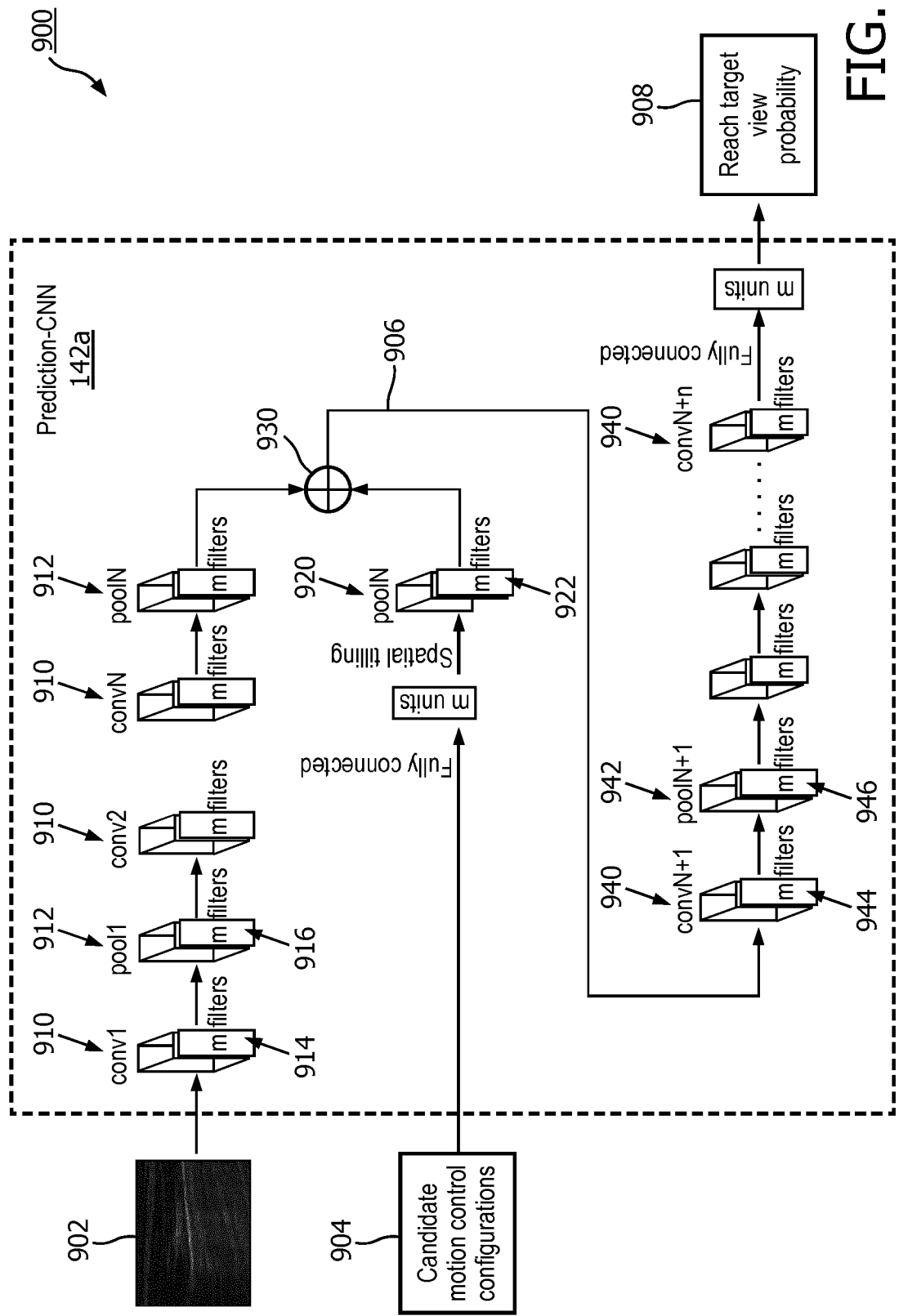
FIG. 9 is a schematic diagram illustrating a configuration for a prediction-convolutional neural network (CNN), according to aspects of the present disclosure.
Figure 10:
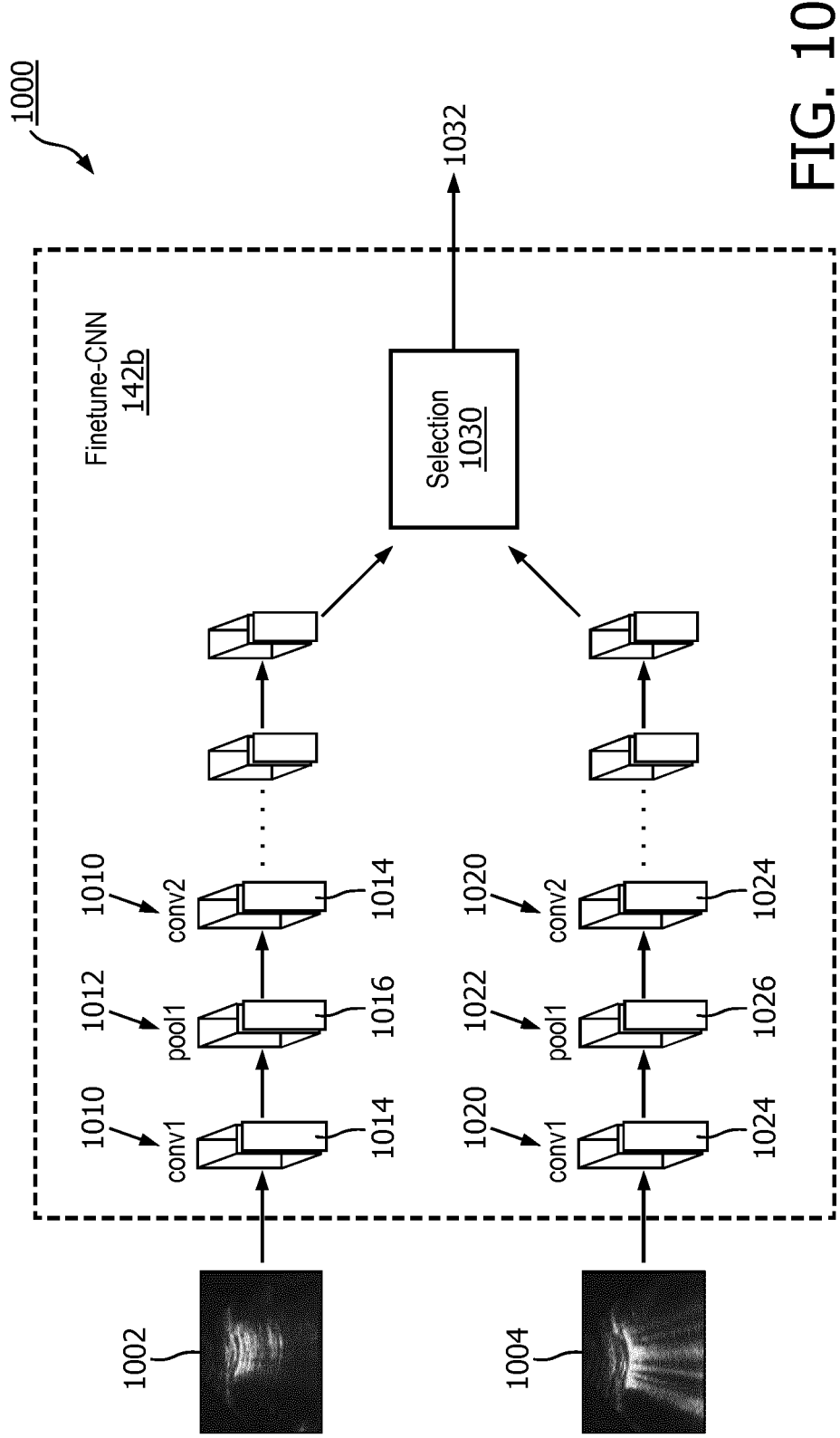
FIG. 10 is a schematic diagram illustrating a configuration for a finetune-CNN, according to aspects of the present disclosure.
Figure 11:
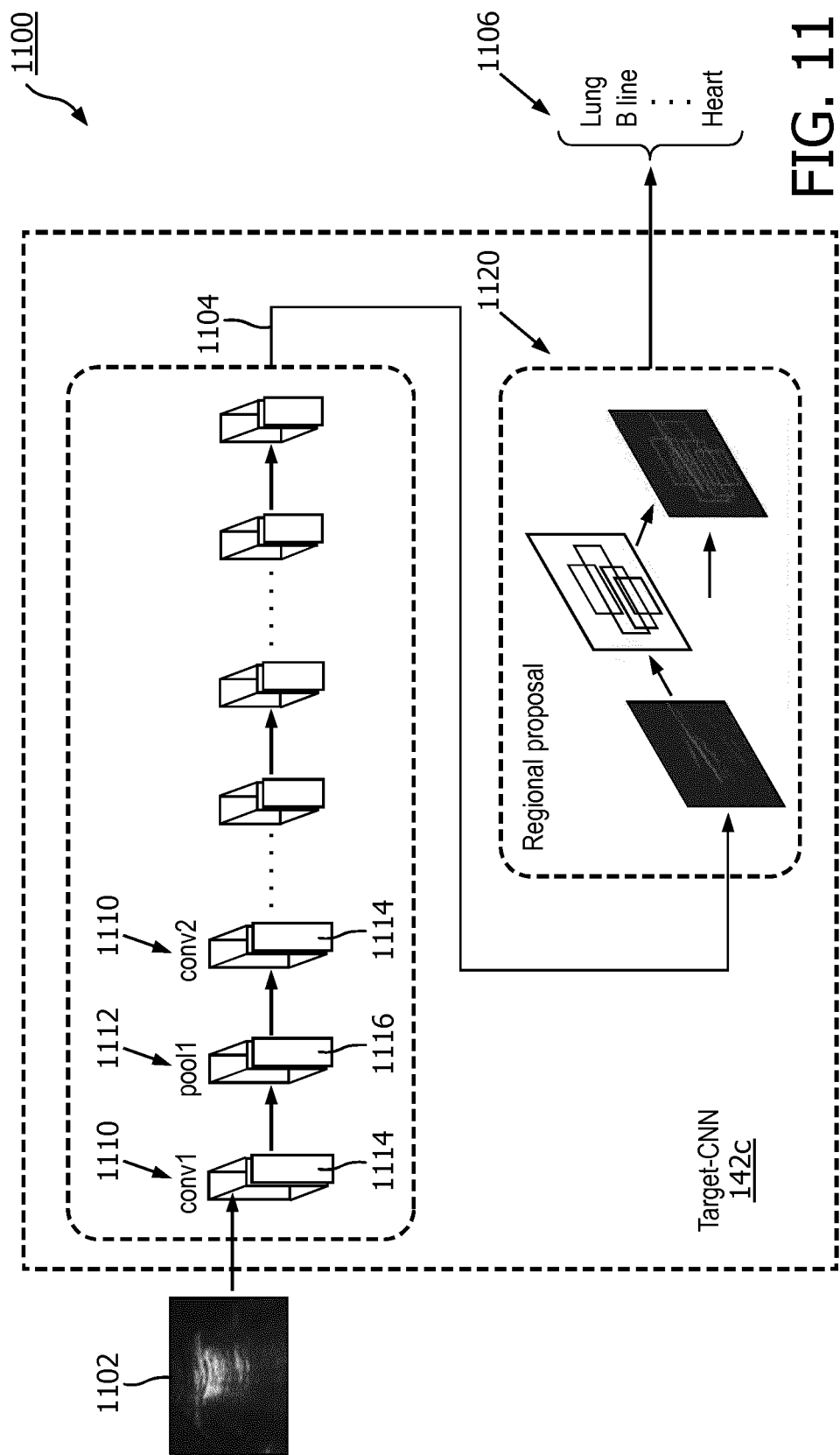
FIG. 11 is a schematic diagram illustrating a configuration for a target-CNN, according to aspects of the present disclosure.

FIGS. 9-11 illustrate internal architectures of the CNNs 142. FIG. 9 is a schematic diagram illustrating a configuration 900 for the prediction-CNN 142a, according to aspects of the present disclosure. The prediction-CNN 142a is used to predict whether a candidate of motion control configurations used for repositioning an imaging component (e.g., the TEE probe 110, the TTE probe 310, and the imaging device 570) will lead to an optimal imaging location for a particular target view (e.g., the target image 830 corresponding to $U_{target}$) given an input image 902. For example, the prediction-CNN 142a may receive a current image 902 (e.g., corresponding to $U_t$) captured by the imaging component located at a current position (e.g., corresponding to $q_t$) with respect to a patient's body (e.g., the patient 102). The prediction-CNN 142a may determine whether a motion control configuration from a set of candidate motion control configurations 904 (e.g., corresponding to $m_t$) can lead the imaging component to the target image view based on the current image. In some embodiments, the set of candidate motion control configurations 904 can include controls for changing an imaging plane within a volumetric ultrasound image. The prediction-CNN 142a may compute a probability 908 (e.g., an output 908) of reaching the target image view for each of candidate motion control configurations and select the candidate motion control configuration with a highest probability of reaching the target image view. The prediction-CNN 142a may include a first set of convolutional layers 910 and pooling layers 912, a spatial tiling layer 920, a summing component 930, a second set of convolutional layers 940 and pooling layers 942.

The prediction-CNN 142a may apply the first set of convolutional layers 910 and pooling layers 912 to the current image 902. Each convolutional layer 910 may include a set of filters 914 configured to extract imaging features from the image 902. Each pooling layer 912 may include a set of filters 916 that may reduce the dimensionality of the extracted imaging features.

The prediction-CNN 142a may apply the spatial tiling layer 920 to each candidate motion control configuration 904. The spatial tiling layer 920 may include a set of filters 922. The spatial tiling layer 920 transforms or maps the candidate motion control configuration 904 to the output spatial dimension of the last pooling layer 912 (e.g., shown as pool N) in the first set. The summing component 930 may compute a sum 906 (e.g., a pointwise summation) between the output of the last pooling layer 912 in the first set and the output of spatial tiling layer 920.

The prediction-CNN 142a may apply the second set of interleaving convolutional layers 940 and the pooling layers 942 to the sum 906. The convolutional layers 940 and the pooling layers 942 may have a substantially similar structure as the convolutional layers 910 and the pooling layers 912, respectively. For example, each convolutional layer 940 may include a set of filters 944 and each pooling layer 942 may include a set of filters 916. The prediction-CNN 142a produces an output 908 representing the probability of reaching the target image view for each candidate motion control configuration 904. Thus, the motion control configuration having the highest probability may be selected from among the candidate motion control configurations 904. The filters 914, 916, 922, 944, and 946 may have any suitable order. The coefficients for the filters 914, 916, 922, 944, and 946 are learnt or trained, as described in greater detail herein.

FIG. 10 is a schematic diagram illustrating a configuration 1000 for the finetune-CNN 142b, according to aspects of the present disclosure. The finetune-CNN 142b is used to select an image having a higher quality from a pair of input images 1002 and 1004. For example, the finetune-CNN 142b may be applied to refine the position of an imaging component (e.g., the TEE probe 110, the TTE probe 310, and the imaging device 570) after the prediction-CNN 142a directed the imaging component to a desired location, as described in greater detail herein. The finetune-CNN 142b includes a first set of convolutional layers 1010 and pooling layers 1012, a second set of convolutional layers 1020 and pooling layers 1022, and a selection component 1030.

The finetune-CNN 142b may apply the first set of interleaving convolutional layers 1010 and pooling layers 1012 to one input image 1002 and the second set of interleaving convolutional layers 1020 and pooling layers 1022 to the other input image 1004. Each convolutional layer 1010 may include a set of filters 1014 and each pooling layer 1012 may include a set of filters 1016. Similarly, each convolutional layer 1020 may include a set of filters 1024 and each pooling layer 1022 may include a set of filters 1026. The selection component 1030 is configured to select an image 1032 having a higher quality from among the pair of images 1002 and 1004. The coefficients for the filters 1014, 1016, 1024, 1026 are learnt or trained, as described in greater detail herein.

FIG. 11 is a schematic diagram illustrating a configuration 1100 for the target-CNN 142c, according to aspects of the present disclosure. The target-CNN 142c is used to qualify the input image 1102 with respect to a target image view. For example, the target-CNN 142c may determine whether an input image 1102 includes a target image view (e.g., the target image view 810 corresponding to $U_{target}$) or a predetermined or selected clinical property (e.g., the LAA 812). In an embodiment, the target-CNN 142c may be trained to recognize a particular anatomical category, such as lungs, a liver, or a heart. The target-CNN 142c includes a set of convolutional layers 1110 and pooling layers 1112 and a regional proposal network 1120. The target-CNN 142c may apply the set of interleaving convolutional layers 1110 and pooling layers 1112 to the input image 1102. Each convolutional layer 1110 may include a set of filters 1114 and each pooling layer 1112 may include a set of filters 1116. The set of convolutional layers 1110 and pooling layers 1112 outputs a feature map 1104.

The regional proposal network 1120 is applied to the feature map 1104. The regional proposal network 1120 may be configured as a CNN. For example, the regional proposal network 1120 may include a set of convolutional layers and pooling layers, each including a set of filters. The regional proposal network 1120 may score the feature map 1104 based on a plurality of anatomical or imaging categories (e.g., heart, lungs, liver, B-line imaging). Thus, the regional proposal network 1120 may classify the input image 1102 into one of the categories based on the highest score. The target-CNN 142c may be trained to detect a particular category (e.g., an image view of a heart) and produces an output 1106 indicating whether the target view or the particular category is detected. For example, the output 1106 may include a value of 1 when the input image 1102 includes the target image view. Conversely, the output 1106 may include a value of 0 when the input image 1102 does not include the target image view. The output 1106 may be referred to as a label or a score. The coefficients for the filters 1114 and 1116 and filters in the regional proposal network 1120 are learnt or trained, as described in greater detail herein.

Figure 12:
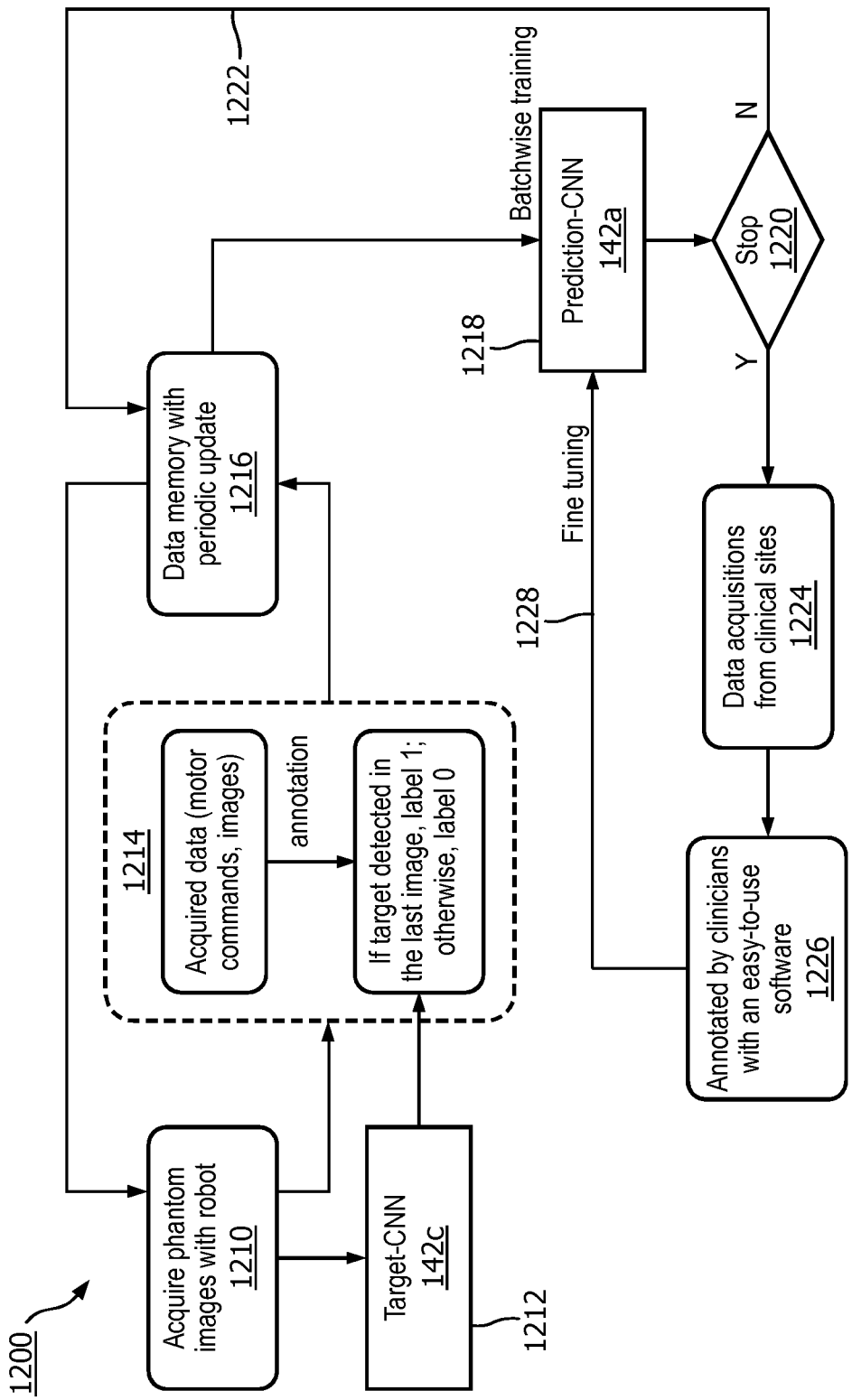
FIG. 12 is a schematic diagram illustrating a scheme for training a prediction-CNN, according to aspects of the present disclosure.
Figure 13:
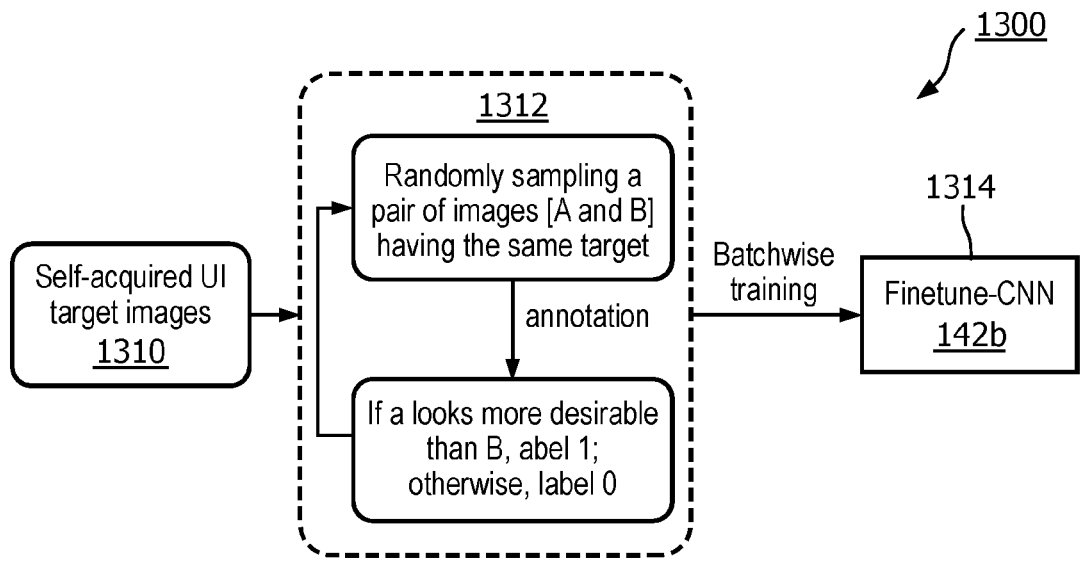
FIG. 13 is a schematic diagram illustrating a scheme for training a finetune-CNN, according to aspects of the present disclosure.
Figure 14:
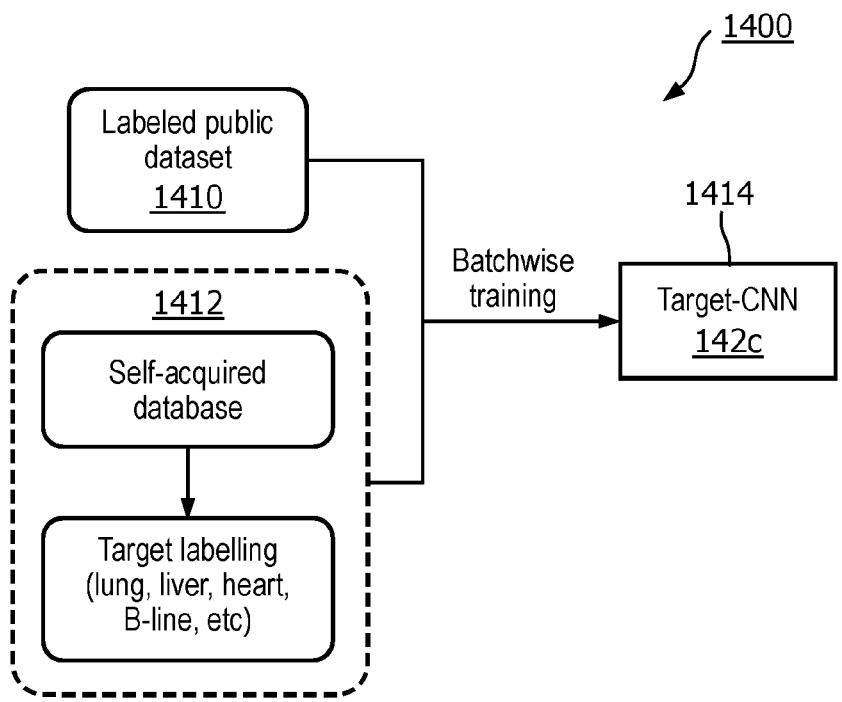
FIG. 14 is a schematic diagram illustrating a scheme for training a target-CNN, according to aspects of the present disclosure.

FIGS. 12-14 illustrate mechanisms for training the CNNs 142. FIG. 12 is a schematic diagram illustrating a scheme 1200 for training the prediction-CNN 142a, according to aspects of the present disclosure. The scheme 1200 may be implemented by the systems 100 or 300. The scheme 1200 provides a more detailed view of the operations performed by the CNN training component 420. The scheme 1200 may be implemented offline using simulated data (e.g., images captured from a phantom) and/or clinical data (e.g., images captured from a patient 102). The scheme 1200 may be used to train the prediction-CNN 142a to predict movements for repositioning an imaging component (e.g., the TEE probe 110, the TTE probe 310, or the imaging device 570) to reach a particular target image view (e.g., the target image view 810). The target image view may include a specific clinical property (e.g., the LAA 812) relevant to a clinical procedure (e.g., an LAAC procedure). The scheme 1200 may train the prediction-CNN 142a incrementally based on a periodically updated associative datasets (e.g., the database 140).

At step 1210, images of a subject's body (e.g., an anatomical phantom) are acquired using the imaging component. The positioning of the imaging component may be controlled by a robotic system (e.g., the robotic system 120, 320, or 520) based on a set of motor commands, motion control configurations, or motion vectors, for example, using similar mechanisms as shown in the scheme 500 described above with respect to FIG. 5.

At step 1212, the target-CNN 142c is applied to the acquired images. The target-CNN 142c determines a score or a label for each acquired image based on the target image view. For example, when the target-CNN 142c detected the target image view (e.g., the desired clinical property) in the acquired image, the target-CNN 142c may output a value of 1. Conversely, when the target-CNN 142c fails to detect the target image view in the acquired image, the target-CNN 142c may output a value of 0. The step 1212 may correspond to the operations of the qualification component 530.

At step 1214, the acquired images are associated with corresponding motor commands and labels to produce associative datasets. For example, each associative dataset may correspond to a data-tuple $d_t$ shown in Equation (2) above. At step 1216, the data memory is updated with the associative datasets. For example, the data memory may correspond to the database 140 stored in the memory 132. The steps of 1210, 1212, 1214, and 1216 may be repeated periodically.

At step 1218, the prediction-CNN 142a receives a batch or a subset of the associative datasets. The subset may be randomly selected from the data memory. In an embodiment, the coefficients for the filters 914, 916, 922, 944, and 946 in the prediction-CNN 142a may be initialized with arbitrary values. The prediction-CNN 142a is applied to each associative dataset in the subset, for example, using forward propagation. The coefficients for the filters 914, 916, 922, 944, and/or 946 may be adjusted, for example, by using backward propagation to minimize the output error (e.g., between the output 908 of the prediction-CNN 142a and the label for the corresponding associative dataset).

At step 1220, a determination is made whether to stop the training or continue the training with more associative datasets. When the determination is to continue with the training, a next subset or batch of associative datasets may be obtained (e.g., randomly selected) from the data memory as shown by the arrow 1222 and the training of the prediction-CNN 142a may be repeated for the next subset of the associative datasets.

At step 1224, when the determination is to stop the training, clinical data (e.g., images of patients captured in a clinical setting) may be obtained to further train the prediction-CNN 142a. At step 1226, a clinician may annotate each clinical image with a label indicating whether a target image view is included in the clinical image. The annotated clinical images may be used to further train or finetune the prediction-CNN 142a as shown by the arrow 1228, for example, to further adjust the coefficients for the filters 914, 916, 922, 944, and/or 946.

FIG. 13 is a schematic diagram illustrating a scheme 1300 for training the finetune-CNN 142b, according to aspects of the present disclosure. The scheme 1300 may be implemented by the systems 100 or 300. The scheme 1300 provides a more detailed view of the operations performed by the CNN training component 420. The scheme 1300 may be implemented offline using images acquired from a phantom and/or clinical data. For example, at step 1310, a set of target images is acquired. The target images may include a particular target image view (e.g., the target image view 810).

At step 1312, image pairs are randomly selected from the set of target images and the image with a higher image quality is selected from each pair.

At step 1314, the finetune-CNN 142b receives a subset of the image pairs and corresponding selections (e.g., indicating the image with the higher quality from an image pair). In an embodiment, the coefficients for the filters 1014, 1016, 1024, and 1026 in the finetune-CNN 142b may be initialized with arbitrary values. The finetune-CNN 142b is applied to each image pair and a corresponding selection, for example, using forward propagation, is made. The coefficients for the filters 1014, 1016, 1024, and/or 1026 may be adjusted, for example, by using backward propagation to minimize the output error (e.g., between the output image 1032 of the finetune-CNN 142b and the selection). The training of the finetune-CNN 142b may be repeated for a next subset of the image pairs and corresponding selections.

FIG. 14 is a schematic diagram illustrating a scheme 1400 for training the target-CNN 142c, according to aspects of the present disclosure. The scheme 1400 may be implemented by the systems 100 or 300. The scheme 1400 provides a more detailed view of the operations performed by the CNN training component 420. The scheme 1400 may be implemented offline using images acquired from a phantom and/or clinical data. For example, at step 1410, a labeled dataset is obtained. The labeled dataset may include images classified into categories (e.g., lungs, heart, liver, B-line, and LAA) and the images may be labeled based on the classifications. At step 1412, acquired labeled images, for example, acquired using a phantom and a robotic system (e.g., the robotic system 120 or 320) or from the database 140 may be obtained.

At step 1414, the target-CNN 142c receives a subset of the labeled datasets and a subset of the acquired labeled images. In an embodiment, the coefficients for the filters 1114 and 1116 in the target-CNN 142c may be initialized with arbitrary values. The target-CNN 142c is applied to the subset of the labeled datasets and the subset of the acquired labeled, for example, using forward propagation. The coefficients for the filters 1114 and/or 1116 may be adjusted, for example, by using backward propagation to minimize the output error (e.g., between the output 1106 of the target-CNN 142c and the classification or label). The training of the target-CNN 142c may be repeated for a next subset of the labeled datasets and a subset of the acquired labeled images.

Figure 15:
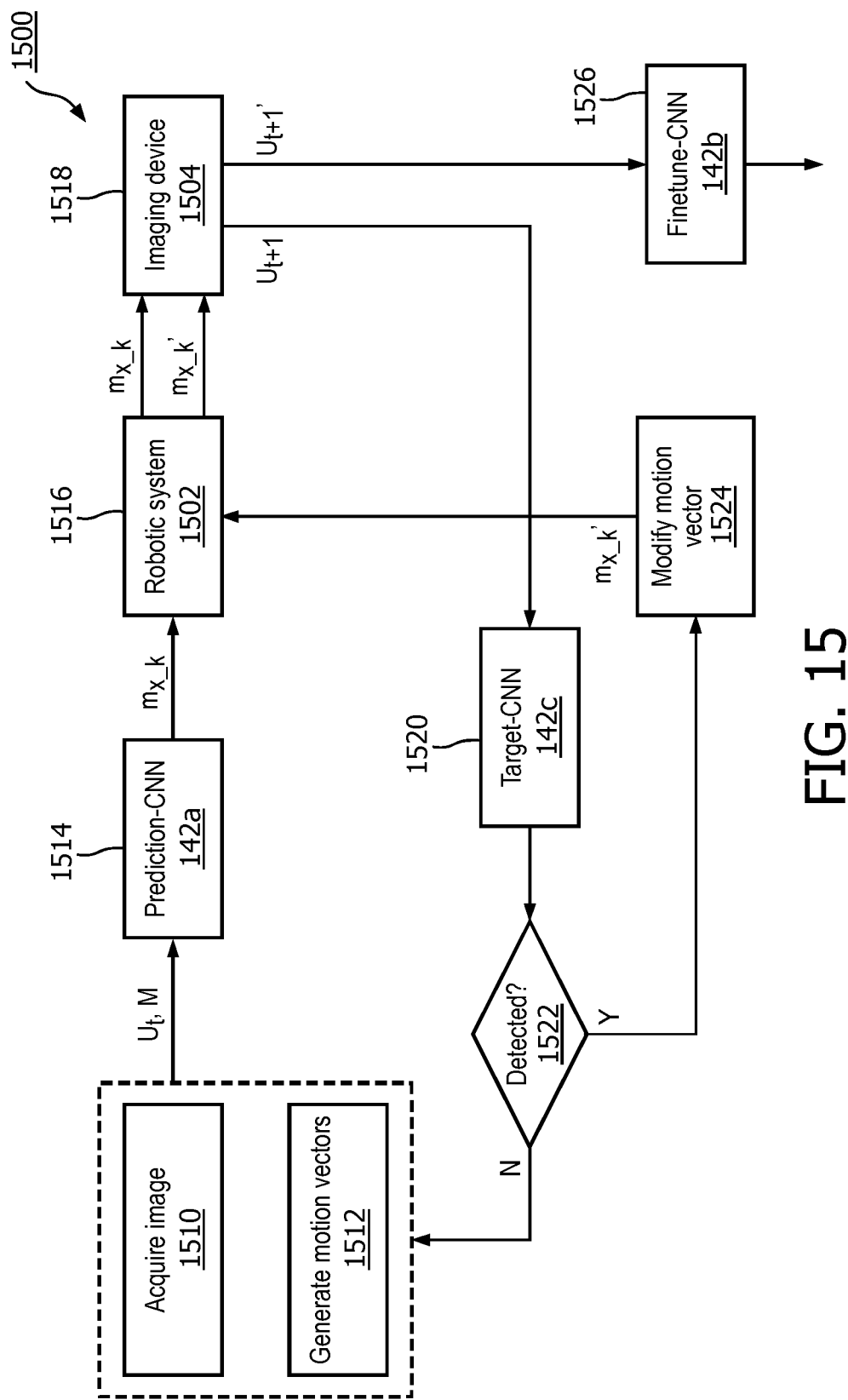
FIG. 15 is a schematic diagram illustrating a scheme for aligning an imaging component to a desired location, according to aspects of the present disclosure.

FIG. 15 is a schematic diagram illustrating a scheme 1500 for aligning an imaging component to a desired location, according to aspects of the present disclosure. The scheme 1500 may be implemented by the systems 100 or 300. The scheme 1500 provides a more detailed view of the operations performed by the CNN application component 430. The scheme 1500 may be used in a clinical setting to obtain images of a patient's anatomy (e.g., the patient 102's heart) prior to a clinical procedure (e.g., an LAAC procedure). The clinician may select a target image view $U_{target}$ (e.g., the target image 830). The clinician may position an imaging device 1504 (e.g., the TEE probe 110, the TTE probe 310, or the imaging device 570) at an initial position $q_t$ in proximity of the patient's anatomy of interest.

At step 1510, an image $U_t$ representative of the patient's anatomy is acquired by the imaging device 1504. At step 1512, a set of motion vectors M is generated, for example, by the processing component 136, within some range of motions arbitrarily chosen by the clinician. The set of motion vectors M may be expressed as shown below:

$$M = \{m_{x\_1}, m_{x\_2}, \ldots, m_{x\_n}\}, \quad (7)$$

where $m_{x\_1}$ to $m_{x\_n}$ are motion vectors, which may be similar to $m_t$ described above in Equations (5) or (6) and may be dependent on the imaging device 1504. For example, the motion vectors $m_{x\_1}$ to $m_{x\_n}$ may include parameters $\alpha$, $\beta$, $\gamma$, and $\omega$ as shown in Equation (5) above when the imaging device 1504 is a TEE probe similar to the TEE probe 110. Alternatively, the motion vectors $m_{x\_1}$ to $m_{x\_n}$ may include parameters $v_{xt}$, $v_{yt}$, $v_{zt}$, $\omega_{xt}$, $\omega_{xt}$, and $\omega_{zt}$ as shown in Equation (6) above when the imaging device 1504 is a TTE probe similar to the TTE probe 310. In some other instances, the set of motion vectors may include parameters for changing an imaging plane within a volumetric image.

At step 1514, the prediction-CNN 142a receives the image $U_t$ and the set of motion vectors M. The prediction-CNN 142a selects or infers the motion vector $m_{x\_k}$ with the highest probability of reaching the target imaging view $U_{target}$ from among the set M. While FIG. 15 illustrates the prediction-CNN 142a selecting one motion vector $m_{x\_k}$, in some embodiments, the prediction-CNN 142a may select a combination of motion vectors (e.g., $\{m_{x\_k1}, m_{x\_k2}, m_{x\_k3}\}$) with the highest probability of reaching the target imaging view $U_{target}$ from among the set M.

At step 1516, a robotic system 1502 (e.g., the robotic systems 120, 320, or 520) receives the determined motion vector $m_{x\_k}$. The robotic system 1502 may reposition the imaging device 1504 based on the motion vector $m_{x\_k}$. The robotic system 1502 may apply a control law, such as a proportional-integral-derivative (PID) control law, to control the positioning of the imaging device 1504. For example, the robotic system 1502 repositions the imaging device 1504 to a next position $q_{t+1}$ based on the motion vector $m_{x\_k}$. At step 1518, the imaging device 1504 may capture a next image $U_{t+1}$ of the patient's anatomy while the imaging device 1504 is at the position $q_{t+1}$.

At step 1520, the target-CNN 142c receives the image $U_{t+1}$. The target-CNN 142c is applied to the image $U_{t+1}$. At step 1522, a determination is made as to whether the target-CNN 142c detected the target image view $U_{target}$ in the image $U_{t+1}$. When the target-CNN 142c fails to detect the target image view in the image $U_{t+1}$, the steps 1510 to 1522 may be repeated.

When the target-CNN 142c detected the target image view $U_{target}$ in the image $U_{t+1}$, the scheme 1500 proceeds to step 1524. At step 1524, the motion vector $m_{x\_k}$ is modified by modifying one or more of the motion parameters by a small amount to produce a modified motion vector, denoted as $m_{x\_k}'$. The scheme 1500 may repeat the steps 1516 and 1518 for the motion vector $m_{x\_k}'$. For example, the robotic system 1502 may reposition the imaging device 1504 to a position $q_{t+n}$ based on the motion vector $m_{x\_k}'$ and the imaging device 1504 may capture an image $U_{t+n}$ of the patient's anatomy while the imaging device 1504 is at the position $q_{t+n}$.

At step 1526, the finetune-CNN 142b may perform a pairwise comparison for the images $U_{t+1}$ and $U_{t+1}'$ and select the image having the higher image quality. In some embodiments, the refining steps of 1524 and 1526 may be repeated. For example, multiple modified motion vectors may be generated and the finetune-CNN 142b may be applied to select the motion vector that leads to an image with the highest quality.

Figure 16:
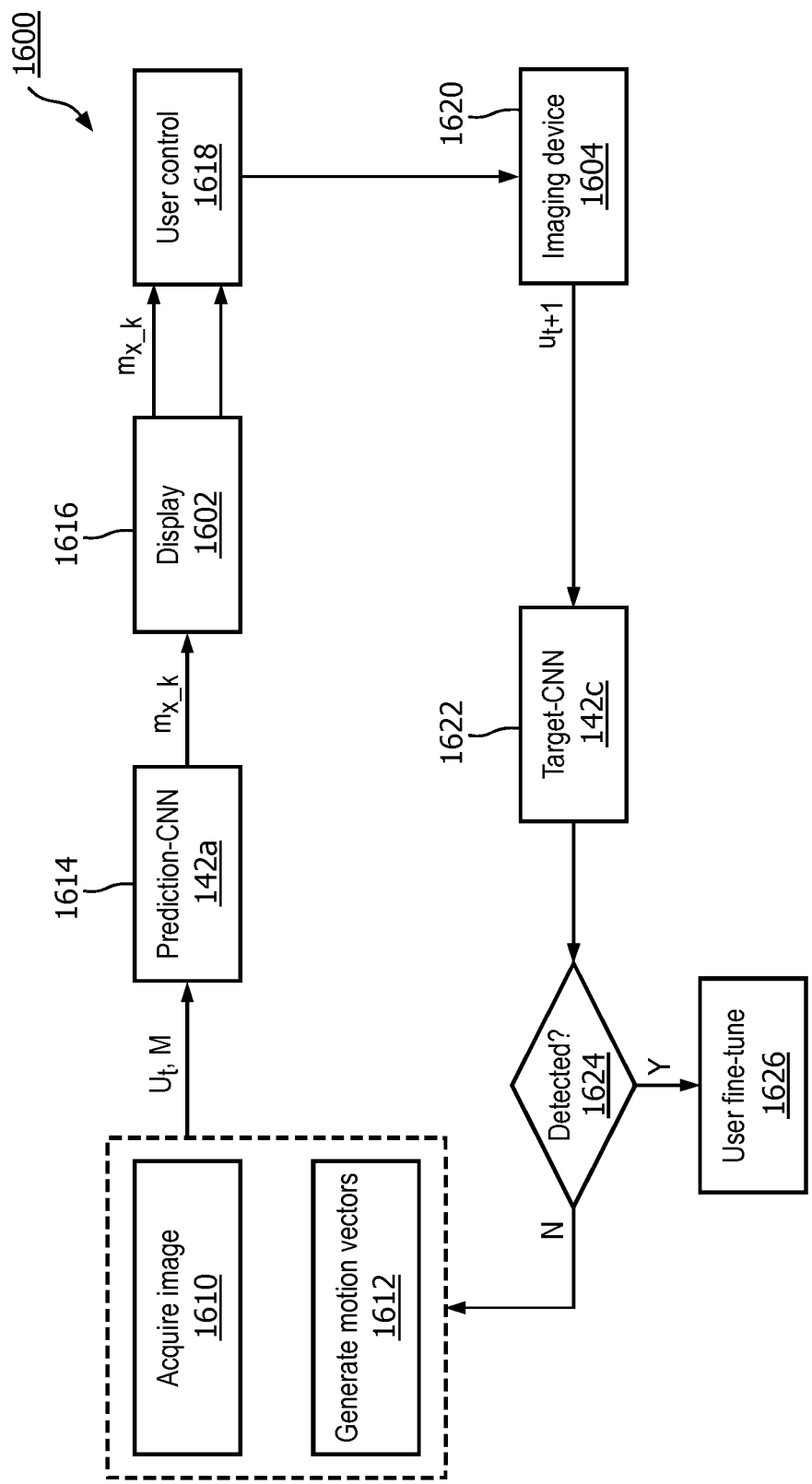
FIG. 16 is a schematic diagram illustrating a scheme for providing guidance to align an imaging component to a desired location, according to aspects of the present disclosure.

FIG. 16 is a schematic diagram illustrating a scheme 1600 for providing guidance to align an imaging component to a desired location, according to aspects of the present disclosure. The scheme 1600 may be implemented by the systems 100 or 300. The scheme 1600 may employ substantially similar mechanisms as in the scheme 1500. For example, the scheme 1600 may be used in a clinical setting to obtain images of a patient's anatomy (e.g., the patient 102's heart) prior to a clinical procedure (e.g., an LAAC procedure). The clinician may select a target image view $U_{target}$ (e.g., the target image view 810). The clinician may position an imaging device 1604 (e.g., the TEE probe 110, the TTE probe 310, or the imaging device 570 or 1504) at a position $q_t$ at a vicinity of the patient's anatomy of interest. The scheme 1600 may apply the prediction-CNN 142a, the finetune-CNN 142b, and/or the target-CNN 142c as described in the scheme 1600. However, the scheme 1600 may provide instructions to the clinician for manual alignment instead of using the robotic system 1502 to automatically align the imaging device 1604.

At step 1610, an image $U_t$ representative of the patient's anatomy is acquired by the imaging device 1604. At step 1612, a set of motion vectors M is generated, for example, by the processing component 136, within some range of motions arbitrarily chosen by the clinician. The set of motion vectors M may be expressed as shown in Equation (7) above.

At step 1614, the prediction-CNN 142a receives the image $U_t$ and the set of motion vectors M. The prediction-CNN 142a selects or infers the motion vector $m_{x\_k}$ with the highest probability of reaching the target imaging view $U_{target}$ from among the set M.

At step 1616, the display 1602 (e.g., the display 134) receives the determined motion vector $m_{x\_k}$ and display instructions instructing the clinician to manipulate the imaging device 1604. The instructions can be in the format of a graphical representation of movements or controls of the imaging device 1604 (e.g., in the UI 144), as described in greater detail herein below.

At step 1618, the clinician may reposition the imaging device 1604 to a next position $q_{t+1}$ based on the instructions displayed on the display 1602.

At step 1620, the imaging device 1604 may capture a next image $U_{t+1}$ of the patient's anatomy while the imaging device 1604 is at the position $q_{t+1}$.

At step 1622, the target-CNN 142c is applied to the image $U_{t+1}$.

At step 1624, a determination is made as to whether the target-CNN 142c detected the target image view $U_{target}$ in the image $U_{t+1}$. When the target-CNN 142c fails to detect the target image view in the image $U_{t+1}$, the steps 1610 to 1624 may be repeated.

When the target-CNN 142c detected the target image view $U_{target}$ in the image $U_{t+1}$, the scheme 1600 proceeds to step 1626. At step 1626, the clinician may refine the position of the imaging device 1604 to obtain an optimal target view.

Figure 17A:
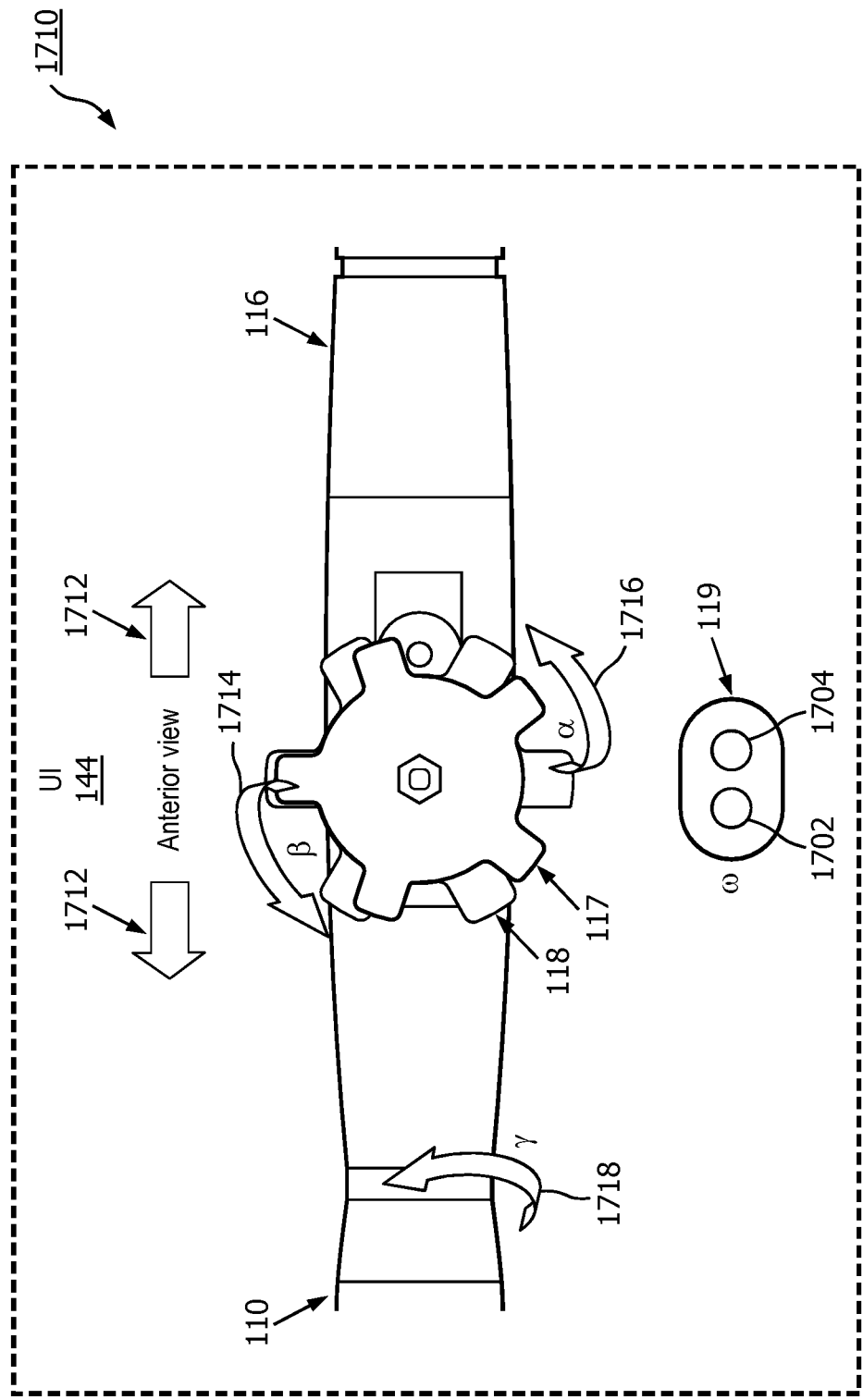
FIG. 17A is a schematic diagram illustrating an imaging component alignment guidance display view, according to aspects of the present disclosure.
Figure 17B:
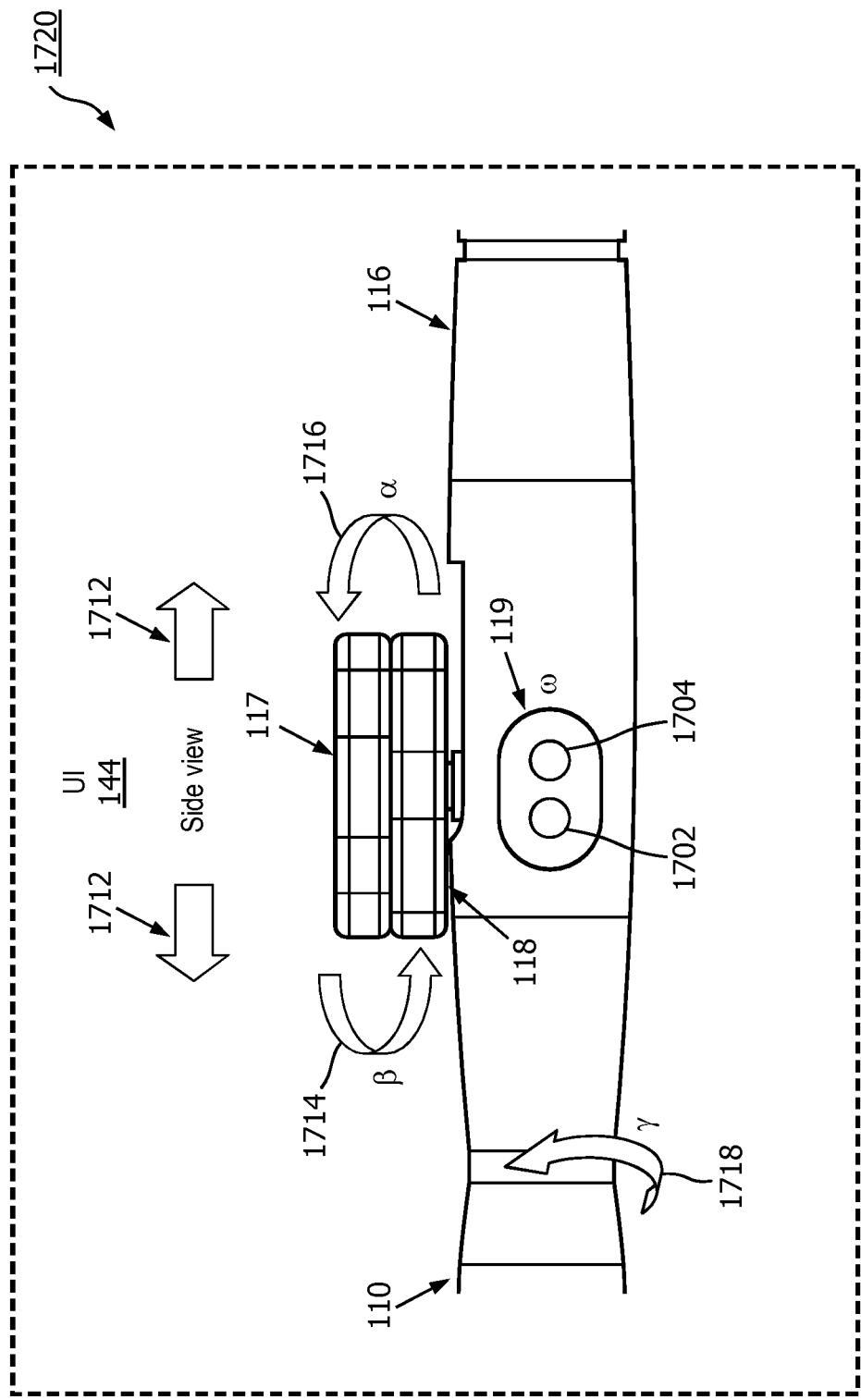
FIG. 17B is a schematic diagram illustrating an imaging component alignment guidance display view, according to aspects of the present disclosure.
Figure 17C:
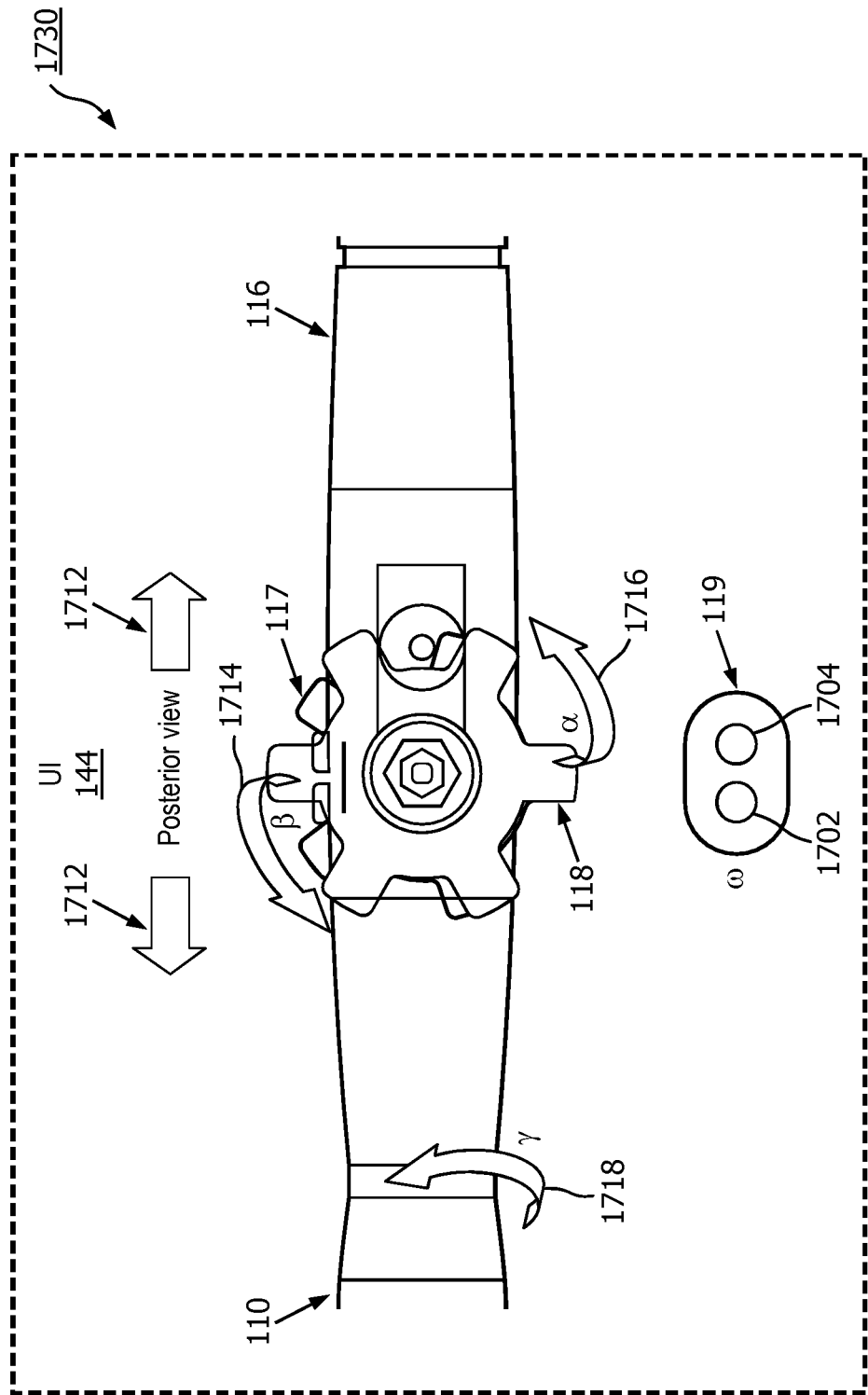
FIG. 17C is a schematic diagram illustrating an imaging component alignment guidance display view, according to aspects of the present disclosure.

FIGS. 17A-17C illustrates various display views for guiding a clinician to align an imaging component (e.g., the TEE probe 110, the TTE probe 310, the imaging device 570, 1504, and 1604) to a desired location for obtaining an optimal target view. FIG. 17A is a schematic diagram illustrating an imaging component alignment guidance display view 1710, according to aspects of the present disclosure. The view 1710 may correspond to a display view on the display 134 in the system 200 or 300 or the display 1602 in the scheme 1600. FIG. 17B is a schematic diagram illustrating an imaging component alignment guidance display view 1720, according to aspects of the present disclosure. FIG. 17C is a schematic diagram illustrating an imaging component alignment guidance display view 1730, according to aspects of the present disclosure. While FIGS. 17A-17C illustrate the UI 144 displaying views of movements for maneuvering the TEE probe 110, the UI 144 may be alternatively configured to display views of movements for maneuvering a TTE probe (e.g., the TTE probe 310) or another imaging device of a different imaging modality.

In the view 1710, the UI 144 shows a graphical representation of an anterior view of the handle 116 of the TEE probe 110 and movements required for directing or aligning the TEE probe to a desired location. In the view 1720, the UI 144 shows a graphical representation of a side view of the handle 116 and movements required for directing or aligning the TEE probe to a desired location. In the view 1730, the UI 144 shows a graphical representation of a posterior view of the handle 116 and movements required for directing or aligning the TEE probe to a desired location. The UI 144 may provide a selection option 1712 to allow a user to select between the different views 1710, 1720, and 1730.

The UI 144 can show a direction (as shown by the arrow 1714) to dial the knob 117 for flexing the TEE probe 110, for example, along a left-right plane with respect to a patient's heart as shown in FIG. 2D. In some embodiments, the UI 144 can also show an amount of movements required based on the parameter β of a corresponding motion vector as shown in Equation (5).

The UI 144 can show a direction (as shown by the arrow 1716) to dial the knob 118 for flexing the TEE probe 110 along an anterior-posterior with respect to a patient's heart as shown in FIG. 2C. In some embodiments, the UI 144 can also show an amount movements required based on the parameter α of a corresponding motion vector as shown in Equation (5).

The UI 144 can further show a direction (as shown by the arrow 1718) to rotate the TEE probe 110, for example, with respect to a longitudinal axis 202 of the TEE probe 110 as shown in FIG. 2A. In some embodiments, the UI 144 can also show an amount of movements required based on the parameter γ of a corresponding motion vector as shown in Equation (5).

The UI 144 can further show a control (e.g., a red button 1702 or a green button 1704) for the switch 119, for example, to enable or disable rotation of an imaging plane of the TEE probe 110 as shown in FIG. 2B. For example, when the switch 119 is set to enable the rotation, the imaging planes may be swept from 0 degree to 180 degrees around an axis with a certain speed and the axis of rotation may be configurable. In some embodiments, the UI 144 can also show an amount of movements required based on the parameter ω of a corresponding motion vector as shown in Equation (5).

Figure 18:
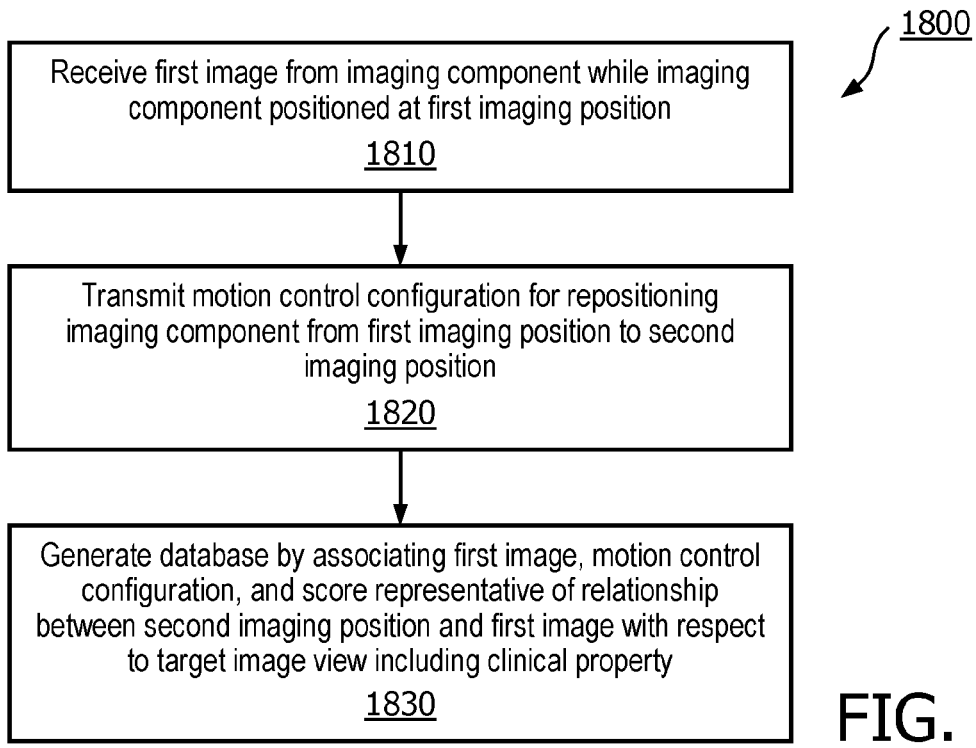
FIG. 18 is a flow diagram of a method of acquiring imaging datasets for training CNNs, according to aspects of the disclosure.

FIG. 18 is a flow diagram of a method 1800 of acquiring imaging datasets for training CNNs, according to aspects of the disclosure. Steps of the method 1800 can be executed by the systems 100 and 300. The method 1800 may employ similar mechanisms as in the scheme 400, 500, 1200, 1500, and 1600 as described with respect to FIGS. 4, 5, 12, 15, and 16, respectively. As illustrated, the method 1800 includes a number of enumerated steps, but embodiments of the method 1800 may include additional steps before, after, and in between the enumerated steps. In some embodiments, one or more of the enumerated steps may be omitted or performed in a different order.

At step 1810, the method 1800 includes receiving a first image from an imaging component or an imaging device while the imaging component is positioned at a first imaging position, for example, via a communication device similar to the communication interface 138. The imaging device can include an ultrasound transducer or an ultrasound transducer array. The imaging device may correspond to the TEE probe 110, the TTE probe 310, or the imaging device 570, 1504, 1604. The first image and the first imaging position may correspond to $U_t$ and $q_t$, respectively, described in the scheme 500. In some instances, the first imaging position may correspond to a particular imaging plane within a volumetric ultrasound image.

At step 1820, the method 1800 includes transmitting a motion control configuration for repositioning the imaging component from the first imaging position to a second imaging position. The motion control configuration and the second imaging position may correspond to $m_t$ and $q_{t+1}$, respectively, described in the scheme 500. In some instances, the first imaging position may correspond to a particular imaging plane within a volumetric ultrasound image.

At step 1830, the method 1800 includes generating a database (e.g., the database 140) by associating the first image, the motion control configuration, and a score (e.g., corresponding to $l_t$ described above) representative of a relationship between the second imaging position and the first image with respect to a target view (e.g., the target image view 810) including a clinical property (e.g., the LAA 812).

In an embodiment, the motion control configuration may include one or more parameters for moving the imaging component to the second imaging position. For example, when the imaging component is a TEE probe 110, the motion control configuration may include the parameters α, β, γ, and ω as shown in Equation (5). Alternatively, when the imaging component is a TTE probe 310, the motion control configuration may include the parameters $v_{xt}$, $v_{yt}$, $v_{zt}$, $\omega_{xt}$, $\omega_{yt}$, and $\omega_{zt}$ as shown in Equation (6) above. The method 1800 can include determining the one or more parameters.

In an embodiment, the method 1800 can include receiving, from the imaging component, a second image (e.g., corresponding to $U_{t+1}$ described above) representative of the subject's body while the imaging component is positioned at the second imaging position; and determining the score based on a comparison between the second image and the target image view. For example, the score may have a value of 1 when the second image matches the target image view. Conversely, the score may have a value of 0 when the second image does not match the target image view. The second image may correspond to $U_{t+1}$ described in the scheme 500.

In an embodiment, the method 1800 can include determining the score based on a comparison between the second imaging position and a target imaging position of the imaging component for obtaining an image of the subject's body corresponding to the target image view. For example, when the subject's body is a phantom, target imaging positions for obtaining particular clinical properties or views may be registered, and thus the score may be based on a comparison between a registered target imaging position and second imaging position.

In an embodiment, the method 1800 can include transmitting the motion control configuration to a robotic system (e.g., the robotic systems 120, 320, 520, and 1502) controlling the imaging component.

Figure 19:
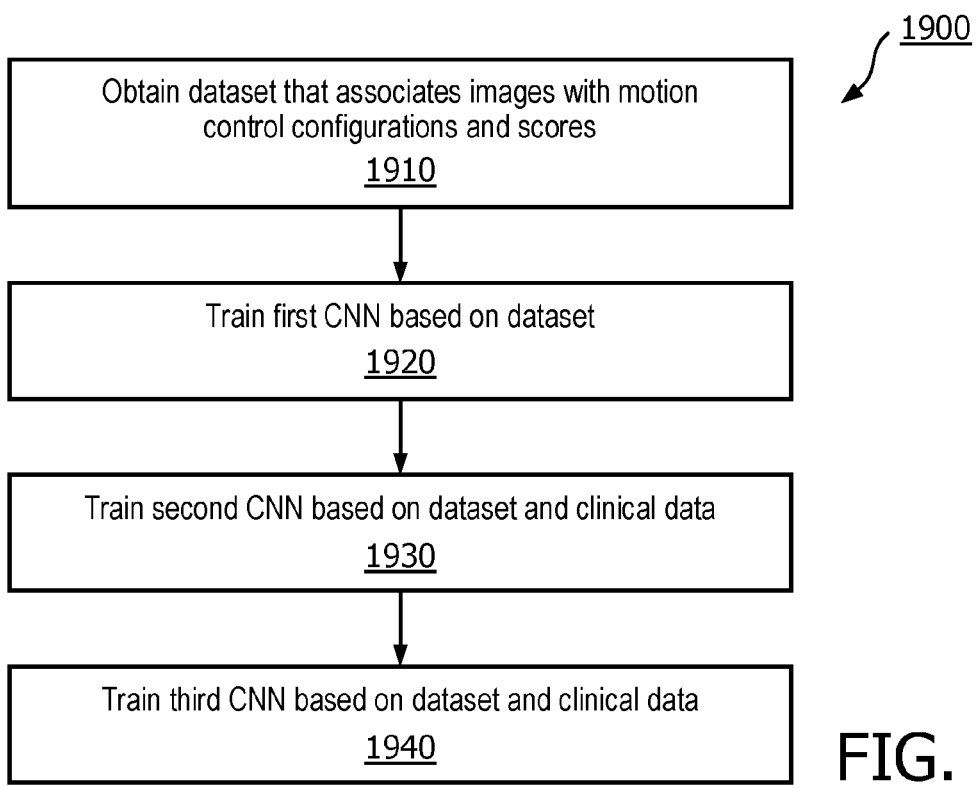
FIG. 19 is a flow diagram of a method of training CNNs, according to aspects of the disclosure.

FIG. 19 is a flow diagram of a method 1900 of training CNNs, according to aspects of the disclosure. Steps of the method 1900 can be executed by the systems 100 and 300. The method 1900 may employ similar mechanisms as in the configurations 900, 1000, and 1100 and the schemes 1200, 1300, and 1400 as described with respect to FIGS. 9, 10, 11, 12, 13, and 14, respectively. As illustrated, the method 1900 includes a number of enumerated steps, but embodiments of the method 1900 may include additional steps before, after, and in between the enumerated steps. In some embodiments, one or more of the enumerated steps may be omitted or performed in a different order.

At step 1910, the method 1900 includes obtaining a dataset that associates images with motion control configuration and scores. The images may be representative of a subject's body (e.g., the patient 102). The images may be captured by an imaging component (e.g., the TEE probe 110, the TTE probe 310, and the imaging devices 570, 1504, and 1604). The motion control configurations are used for repositioning the imaging component. The scores are representative of relationships between the plurality of motion control configurations and the plurality of images with respect to a target image view (e.g., the target image view 810) including a clinical property (e.g., the LAA 812). In an embodiment, the dataset may correspond to D in Equation (4) above. The images, the motion control configuration, and the scores may correspond to $U_t$, $m_t$, and $l_t$, respectively, in Equation (2) above.

At step 1920, the method 1900 includes training a first CNN (e.g., the prediction-CNN 142a) based on the dataset.

At step 1930, the method 1900 includes training a second CNN (e.g., the finetune-CNN 142b) based on the dataset or clinical data.

At step 1940, the method 1900 includes training a third CNN (e.g., the target-CNN 142c) based on the dataset or clinical data.

In an embodiment, the first CNN may have a configuration similar to the configuration 900. For example, the method 1900 can train the first CNN by applying at least a first convolutional layer (e.g., the convolutional layers 910) and a first pooling layer (e.g., the pooling layers 912) to a first image (e.g., the image 902) of the plurality of images. The method 1900 can include determining a sum based on an output of the first pooling layer and a first motion control configuration of the plurality of motion control configurations associated with the first image. The method 1900 can include applying at least a second convolutional layer (e.g., the convolutional layers 940) and a second pooling layer (e.g., the pooling layers 942) to the sum. The method 1900 can include adjusting a coefficient (e.g., the coefficients of the filters 914, 916, 922 944, 946) in at least one of the first convolutional layer, the first pooling layer, the second convolutional layer, or the second pooling layer based on an output (e.g., the output 908) of the second pooling layer and a first score of the plurality of scores associated with the first image. The trained first CNN can predict a motion control configuration for obtaining an image including the clinical property based on an input image.

In an embodiment, the second CNN may have a configuration similar to the configuration 1000. The method 1900 can include obtaining an indication indicating that a first image (e.g., the image 1002) of the plurality of images has a higher quality than a second image (e.g., the image 1004) of the plurality of images with respect to the target image view. The method 1900 can train the second CNN by applying at least a first convolutional layer (e.g., the convolutional layers 1010) and a first pooling layer (e.g., the pooling layers 1012) to the first image. The method 1900 can include applying at least a second convolutional layer (e.g., the convolutional layers 1020) and a second pooling layer (e.g., the pooling layers 1022) to the second image. The method 1900 can include adjusting a coefficient (e.g., the coefficients of the filters 1014, 1016, 1024, and 1026) in at least one of the first convolutional layer, the first pooling layer, the second convolutional layer, or the second pooling layer based on an output of the first pooling layer, an output of the second pooling layer, and the indication (e.g., the image 1032). The trained second CNN can select a higher quality image from among a pair of input images with respect to the target image view In an embodiment, the third CNN may have a configuration similar to the configuration 1100. The method 1900 can include obtaining a candidate image and a classification classifying the candidate image into a first category of a plurality of categories of anatomical parts. The method 1900 can train the third CNN based on the candidate image and the classification of the first category. The trained third CNN can classify an input image into one of the plurality of categories.

Figure 20:
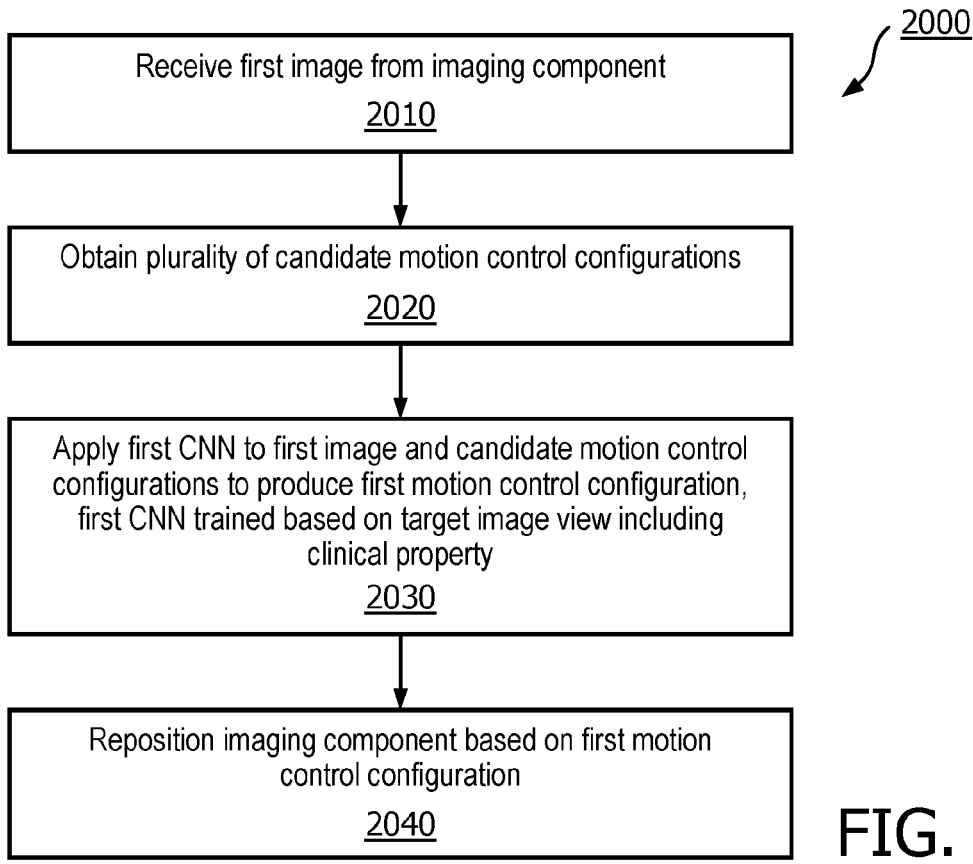
FIG. 20 is a flow diagram of a method of applying CNNs to align an imaging component to a desired location, according to aspects of the disclosure.

FIG. 20 is a flow diagram of a method 2000 of applying CNNs, according to aspects of the disclosure. Steps of the method 2000 can be executed by the systems 100 and 300. The method 1900 may employ similar mechanisms as in the schemes 400, 1500, and 1600 as described with respect to FIGS. 4, 15, and 16, respectively. As illustrated, the method 2000 includes a number of enumerated steps, but embodiments of the method 2000 may include additional steps before, after, and in between the enumerated steps. In some embodiments, one or more of the enumerated steps may be omitted or performed in a different order.

At step 2010, the method 2000 includes receiving a first image (e.g., the image 902) from an imaging component. The images may be representative of a subject's body (e.g., the patient 102). The images may be captured by an imaging component (e.g., the TEE probe 110, the TTE probe 310, and the imaging devices 570, 1504, and 1604) while the imaging component is positioned at a first imaging position. The first imaging position may refer to a particular physical location (e.g., $q_t$ as described in the scheme 500) of the ultrasound imaging component and/or a particular imaging plane within a volumetric ultrasound image.

At step 2020, the method 2000 includes obtaining a plurality of candidate motion control configurations (e.g., the candidate motion control configurations 904) for repositioning the imaging component.

In an embodiment, the plurality of candidate motion control configurations can be obtained by randomly sampling a set of movement parameters for repositioning the imaging component. For example, when the imaging component is a TEE probe 110, the motion control configuration can include the parameters α, β, γ, and co as shown in Equation (5). Alternatively, when the imaging component is a TTE probe 310, the motion control configuration can include the parameters $v_{xt}$, $v_{yt}$, $v_{zt}$, $\omega_{xt}$, $\omega_{yt}$, and $\omega_{zt}$ as shown in Equation (6) above.

At step 2030, the method 2000 includes applying a first CNN (e.g., the prediction-CNN 142a) to the first image and the candidate motion control configurations to produce a first motion control configuration (e.g., the configuration 904). The first CNN is trained based on a target image view (e.g., the target image view 810) including a clinical property (e.g., the LAA 812).

At step 2040, the method 2000 includes repositioning the imaging component based on the first motion control configuration. For example, the imaging component is repositioned from the first imaging position to a second imaging position. The second imaging position may refer to a particular physical location (e.g., $q_{t+1}$ as described in the scheme 500) of the ultrasound imaging component and/or a particular imaging plane within a volumetric ultrasound image.

In an embodiment, the applying the first CNN includes applying at least a first convolutional layer (e.g., the convolutional layers 910) and a first pooling layer (e.g., the pooling layers 912) to the first image. The applying the first CNN can further includes determining a sum based on an output of the first pooling layer and a first candidate motion control configuration of the plurality of candidate motion control configurations. The applying the first CNN can further includes applying at least a second convolutional layer (e.g., the convolutional layers 940) and a second pooling layer (e.g., the pooling layers 942) to the sum. The applying the first CNN can further includes determining the first motion control configuration based on an output of the last prediction layer.

In an embodiment, the method 2000 further includes applying a second CNN (e.g., the target-CNN 142c) to the second image to qualify the second image with respect to the target image view. When the second CNN indicates that the second image is disqualified, the method 2000 can re-apply the first CNN to the second image to produce a second motion control configuration for repositioning the imaging component from the second imaging position to a third imaging position and re-apply the second CNN to qualify the third image with respect to the target image view. The method 2000 can be repeat the re-applying of the first CNN and the second CNN steps until the imaging component can capture the target image view.

Alternatively, when the second CNN indicates that the second image is qualified, the method 2000 can adjust the second imaging position based on a third CNN (e.g., the finetune-CNN 142b). For example, the method 2000 can reposition the imaging component to a third imaging position and capture a third image of the subject's body while the imaging component is at the third imaging position. The method 2000 can apply the third CNN to the second image and the third image. The method 2000 can select the second image or the third image based on an output of the third CNN.

In an embodiment, the method 2000 can send an instruction to a robotic system (e.g., the robotic systems 120, 320, or 1502) to instruct the robotic system to reposition the imaging component to the second imaging position based on the first motion control configuration.

Figure 21:
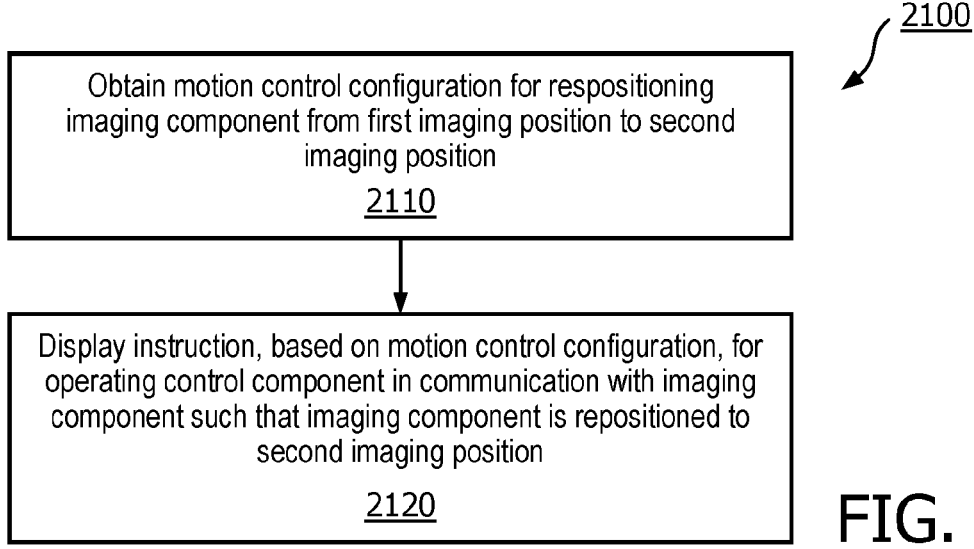
FIG. 21 is a flow diagram of a method of providing imaging component alignment guidance based on CNNs, according to aspects of the disclosure.

FIG. 21 is a flow diagram of a method 2100 of providing imaging component alignment guidance based on CNNs, according to aspects of the disclosure. Steps of the method 2100 can be executed by the systems 100 and 300. The method 2100 may employ similar mechanisms as in the schemes 400 and 1600 and the views 1710, 1720, and 1730 as described with respect to FIGS. 4, 16, 17A, 17B, and 17C, respectively. As illustrated, the method 2100 includes a number of enumerated steps, but embodiments of the method 2100 may include additional steps before, after, and in between the enumerated steps. In some embodiments, one or more of the enumerated steps may be omitted or performed in a different order.

At step 2110, the method 2100 includes obtaining a motion control configuration for repositioning an imaging component or an imaging device from a first imaging position to a second imaging position with respect to a subject's body (e.g., the patient 102). The imaging device can include an ultrasound transducer or an ultrasound transducer array. The imaging device may correspond to the TEE probe 110, the TTE probe 310, or the imaging device 570, 1504, 1604. The motion control configuration can be obtained based on a predictive network (e.g., the CNNs 142), an image of the subject's body captured while the imaging component is positioned at the first imaging position, and a target image view (e.g., the target image view 810) including a clinical property (e.g., the LAA 812). The image may correspond to the image $U_t$ in the scheme 1600. The motion control configuration may correspond to the motion vector $m_{x\_k}$ in the scheme 1600. The first and second imaging positions may refer to particular physical locations (e.g., $q_t$ and $q_{t+1}$ as described in the scheme 500) of the ultrasound imaging component and/or particular imaging planes within a volumetric ultrasound image.

At step 2120, the method 2100 includes displaying an instruction, based on the motion control configuration, for operating a control component (e.g., the handle 116) in communication with the imaging component such that the imaging component is repositioned to the second imaging position.

The method 2100 can display the instruction using similar displays as shown in the views 1710, 1720, and 1730. For example, the method 2100 can display a graphical view of the control component and a visual indicator indicating at least one of a direction of a movement for operating the control component or an amount of the movement. The graphical view can include a perspective view of the control component.

In an embodiment, the method 2100 can receive a request for a first view of a plurality of views of the control component and switch the graphical view from a current view of the plurality of views to the first view in response to the request. The plurality of views can include at least one of an anterior view of the control component, a sideview of the control component, or a posterior view of the control component. The control component can include at least one of a first sub-component (e.g., the knob 117) that controls a movement of the imaging component along a left-right plane of the subject's body, a second sub-component (e.g., the knob 118) that controls a movement of the imaging component along anterior-posterior plane of the subject's body, or a third sub-component (e.g., the switch 119) that controls an orientation of an imaging plane of the imaging component. The motion control configuration can include at least one of a first parameter for operating the first sub-component, a second parameter for operating the second sub-component, a third parameter for operating the third sub-component, or a fourth parameter for rotating the imaging component with respect to an axis of the imaging component. The first parameter, the second parameter, the third parameter, and the fourth parameter may correspond to the parameters $\alpha$, $\beta$, $\omega$, and $\gamma$ of Equation (5) shown above. The displaying can include displaying a visual indicator including at least one of an arrow (e.g., the arrows 1714, 1716, and 1718) or an on/off indicator (e.g., the buttons 1702 and 1704). While the method 2100 is described in the context of a TEE probe, similar mechanisms can be applied to provide alignment guidance for a TTE probe or an imaging device of another imaging modality.

Figure 22:
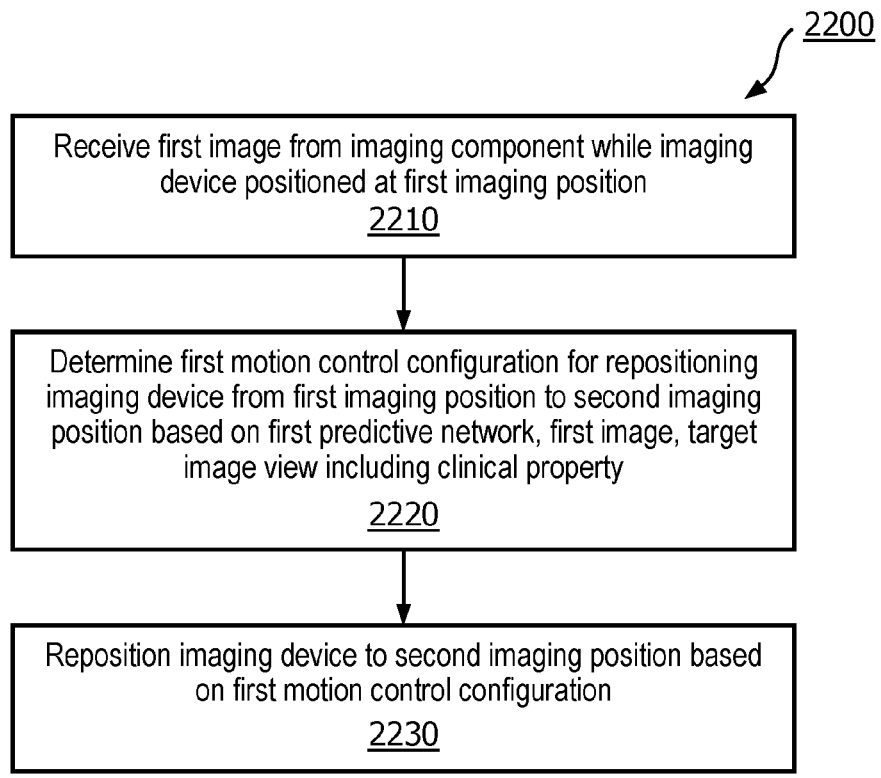
FIG. 22 is a flow diagram of a method of automating a medical examination, according to aspects of the disclosure.

FIG. 22 is a flow diagram of a method 22000 of automating a medical examination, according to aspects of the disclosure. Steps of the method 2200 can be executed by the systems 100 and 300. The method 2200 may employ similar mechanisms as in the schemes 400, 1500, and 2000 as described with respect to FIGS. 4, 15, and 20, respectively. As illustrated, the method 2200 includes a number of enumerated steps, but embodiments of the method 2200 may include additional steps before, after, and in between the enumerated steps. In some embodiments, one or more of the enumerated steps may be omitted or performed in a different order.

At step 2210, the method 2200 includes receiving a first image from an imaging device while the imaging device is positioned at a first imaging position with respect to a subject's body (e.g., the patient 102). The first image may be received via a communication device similar to the communication interface 138. The image may be representative of the subject's body. The imaging device can include an ultrasound transducer or an ultrasound transducer array. The imaging device may correspond to the TEE probe 110, the TTE probe 310, or the imaging device 570, 1504, 1604.

At step 2220, the method 2200 includes determining a first motion control configuration for repositioning the imaging device from the first imaging position to a second imaging position based on a first predictive network (e.g., the CNN 142a), the first image, and a target image view (e.g., the target image view 810) including a clinical property (e.g., the LAA 812). The first and second imaging positions may refer to particular physical locations (e.g., $q_r$ and $q_{r+1}$ as described in the scheme 500) of the ultrasound imaging component and/or particular imaging planes within a volumetric ultrasound image.

At step 2230, the method 2200 includes repositioning, by a robotic system coupled to the imaging device, the imaging device to the second imaging position based on the first motion control configuration. The robotic system may be similar to the robotic systems 120 and 320.

In an embodiment, the method 2200 further includes receiving, from the imaging device, a second image representative of the subject's body while the imaging device is positioned at the second imaging position with respect to the subject's body and determining whether the second image includes the clinical property of the target image view based on a second predictive network (e.g., the CNN 142b).

When the second image is determined not to include the clinical property of the target image view, the method 2200 further includes determining a second motion control configuration, repositioning the imaging device to a third imaging position based on the second motion control configuration, and receiving a third image representative of the subject's body while the imaging device is positioned at the third imaging position with respect to the subject's body. The method 2200 can further include repeating the determining a motion control configuration (e.g., second, third, fourth, fifth, n-th motion control configuration), the repositioning the imaging device to an imaging position (e.g., third, fourth, fifth, n-th imaging position), and receiving an image (e.g., third, fourth, fifth, n-th image) until an image including the clinical property of the target image view is received from the imaging device.

When the second image is determined to include the clinical property of the target image view, the method 2200 can further include determining an adjustment for the second imaging position. The method 2200 can further include repositioning, by the robotic system, the imaging device to a third imaging position based on the adjustment, receiving, from the imaging device, a third image representative of the subject's body while the imaging device is positioned at the third imaging position with respect to the subject's body, and selecting a target imaging position from among the second imaging position and the third imaging position, based on a third predictive network. The method 2200 can further include receiving, from the imaging device, a fourth image representative of the subject's body while the imaging device is positioned at the selected target imaging position, and determining a medical examination result associated with the clinical property based on the fourth image.

In an embodiment, the method 2200 can further include determining a plurality of candidate motion control configurations by sampling a set of movements for repositioning the imaging device. The determination of the first motion control configuration can further include selecting the first motion control configuration from the plurality of candidate motion control configurations based on the first predictive network, the first image, and the target image view.

In an embodiment, the first predictive network is trained by providing a plurality of images obtained by the imaging device from at least two imaging positions to obtain the target image view, obtaining a plurality of motion control configurations based on an orientation or a movement of the imaging device associated with the at least two imaging positions, and assigning a score to a relationship between the plurality of motion control configurations and the plurality of images with respect to the target image view, for example, as described in the method 1900.

Aspects of the present application can provide several benefits. For example, the use of a robotic system to acquire imaging datasets can generate and provide consistent movements and/or controls for repositioning imaging components. The use of automatic annotations (e.g., by applying a target-CNN) can eliminate the need for expert radiologists for the annotations and remove user variability in the annotations. The use of the robotic system in conjunction with the automatic annotations allow for consistent large-scale image dataset acquisition, and thus may improve the accuracies of the predictive networks and subsequent use of the predictive networks in predicting optimal movements and/or controls for repositioning the imaging components. In addition, the use of the robotic system in conjunction with the automatic annotations can allow for acquisition using multiple different anatomical phantoms (e.g., multiple cardiac phantoms) and/or multiple different imaging components (e.g., multiple TEE probes) or medical imaging systems, and thus may increase the diversity of the datasets. The use of acquiring image datasets under a combination of controlled environments and clinical environments can allow for data diversity in the acquisition. The disclosed embodiments can automatically, consistently, and, systematically collect large-scale imaging datasets with annotations suitable for training deep learning predictive networks. While the disclosed embodiments are described in the context of acquiring large-scale image datasets using a TEE probe or a TTE probe, the disclosed embodiments can be applied to acquire large-scale image datasets with any imaging component of any imaging modality.

Further embodiments of the present disclosure include a medical ultrasound image system. The system includes an interface in communication with an ultrasound imaging component and configured to receive a first image representative of a subject's body from the ultrasound imaging component while the ultrasound imaging component is positioned at a first imaging position with respect to the subject's body; and transmit a motion control configuration for repositioning the ultrasound imaging component from the first imaging position to a second imaging position; a processing component in communication with the interface and configured to generate a database by associating the first image, the motion control configuration, and a score representative of a relationship between the second imaging position and the first image with respect to a target image view including a clinical property; and a memory in communication with the processing component and configured to store the database to facilitate training of a predictive network for alignment of the ultrasound imaging component.

In some embodiments, the motion control configuration includes one or more parameters for repositioning the ultrasound imaging component to the second imaging position. In some embodiments, the processing component is further configured to determine the one or more parameters. In some embodiments, the processing component is further configured to determine the one or more parameters based on a random function. In some embodiments, the one or more parameters includes at least one of a parameter for moving the ultrasound imaging component along a left-right plane of the subject's body, a parameter for moving the ultrasound imaging component along an anterior-posterior plane of the subject's body, a parameter for orienting an imaging plane of the ultrasound imaging component, or a parameter for rotating the ultrasound imaging component with respect to an axis of the ultrasound imaging component. In some embodiments, the ultrasound imaging component is a transesophageal echocardiography (TEE) probe. In some embodiments, the one or more parameters include at least one of a linear velocity parameter or an angular velocity parameter for moving the ultrasound imaging component. In some embodiments, the ultrasound imaging component is a transthoracic echocardiography (TTE) probe. In some embodiments, the interface is further configured to receive a second image representative of the subject's body while the ultrasound imaging component is positioned at the second imaging position, and wherein the processing component is further configured to determine the score based on a comparison between the second image and the target image view. In some embodiments, the processing component is further configured to determine the score based on a comparison between the second imaging position and a target imaging position of the ultrasound imaging component for obtaining an image of the subject's body corresponding to the target image view. In some embodiments, the score indicates a success when the second imaging position corresponds to a target imaging position of the ultrasound imaging component for obtaining an image of the subject's body corresponding to the target image view. In some embodiments, the processing component is further configured to determine the motion control configuration, and wherein the interface is further configured to transmit the motion control configuration to a robotic system controlling the ultrasound imaging component.

Further embodiments of the present disclosure include a method of medical ultrasound image data acquisition. The method includes receiving, from an ultrasound imaging component, a first image representative of a subject's body while the ultrasound imaging component is positioned at a first imaging position with respect to the subject's body; transmitting a motion control configuration for repositioning the ultrasound imaging component from the first imaging position to a second imaging position; and generating a database by associating the first image, the motion control configuration, and a score representative of a relationship between the second imaging position and the first image with respect to a target image view including a clinical property.

In some embodiments, the motion control configuration includes one or more parameters for moving the ultrasound imaging component to the second imaging position. In some embodiments, the method further comprises determining the one or more parameters. In some embodiments, the ultrasound imaging component is a transesophageal echocardiography (TEE) probe, and wherein the one or more parameters includes a least one of a parameter for moving the ultrasound imaging component along a left-right plane of the subject's body, a parameter for moving the ultrasound imaging component along anterior-posterior plane of the subject's body, a parameter for orienting an imaging plane of the ultrasound imaging component, or a parameter for rotating the ultrasound imaging component with respect to an axis of the ultrasound imaging component. In some embodiments, the ultrasound imaging component is a transthoracic echocardiography (TTE) probe, and wherein the one or more parameters includes a least one of a linear velocity parameter or an angular velocity parameter for moving the ultrasound imaging component towards the second imaging position. In some embodiments, the method further comprises receiving, from the ultrasound imaging component, a second image representative of the subject's body while the ultrasound imaging component is positioned at the second imaging position; and determining the score based on a comparison between the second image and the target image view. In some embodiments, the method further comprises determining the score based on a comparison between the second imaging position and a target imaging position of the ultrasound imaging component for obtaining an image of the subject's body corresponding to the target image view. In some embodiments, the transmitting the motion control configuration includes transmitting the motion control configuration to a robotic system controlling the ultrasound imaging component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
an ultrasound imaging probe;
a memory;
a processor configured for communication with the ultrasound imaging probe and the memory, wherein the processor is configured to:
control, with an output of a motion control configuration, the ultrasound imaging probe to be physically repositioned from a first imaging position to a second imaging position;
control the ultrasound imaging probe to obtain an ultrasound image representative of a subject's body while the ultrasound imaging probe is positioned at the second imaging position;
retrieve a target imaging position for the ultrasound imaging probe from the memory;
determine a score based on a comparison between the second imaging position and the target imaging position;
generate a data tuple comprising the ultrasound image, the motion control configuration, and the score; and
store the data tuple in the memory and train a predictive network for aligning the imaging probe to the target imaging position based on the data tuple.

2. The apparatus of claim 1, wherein the motion control configuration includes one or more parameters for repositioning the ultrasound imaging probe to the second imaging position.

3. The apparatus of claim 2, wherein the processor is further configured to determine the one or more parameters.

4. The apparatus of claim 3, wherein the processor is further configured to determine the one or more parameters based on a random function.

5. The apparatus of claim 2, wherein the one or more parameters correspond to one or more of a movement of the ultrasound imaging probe along a left-right plane of the subject's body, a movement of the ultrasound imaging probe along an anterior-posterior plane of the subject's body, an orientation of an imaging plane of the ultrasound imaging probe, or a rotation of the ultrasound imaging probe with respect to an axis of the ultrasound imaging probe.

6. The apparatus of claim 5, wherein the ultrasound imaging probe is a transesophageal echocardiography (TEE) probe.

7. The apparatus of claim 2, wherein the one or more parameters correspond to at least one of a linear velocity or an angular velocity for ultrasound imaging probe.

8. The apparatus of claim 7, wherein the ultrasound imaging probe is a transthoracic echocardiography (TTE) probe.

9. The apparatus of claim 1, wherein the processor is configured to:
determine a plurality of motion control configurations;
control, with an output of the plurality of motion control configuration, the ultrasound imaging probe to be physically repositioned to a plurality of imaging positions;
control the ultrasound imaging probe to obtain a plurality of ultrasound images representative of a subject's body while the ultrasound imaging probe is positioned at the plurality of imaging positions;
retrieve a target imaging position for the ultrasound imaging probe from the memory;
determine a plurality of scores based on a comparison between the plurality of imaging positions and the target imaging position;
generate a plurality of data tuples, each data tuple comprising one of each of the plurality of ultrasound images, the plurality of motion control configurations, and the plurality of scores; and
store the plurality of data tuples in the memory.

10. The apparatus of claim 9, wherein the plurality of data tuples are stored in the memory as an ordered sequence, the ordering based on the sequence of imaging positions.

11. The apparatus of claim 9, wherein each of the plurality motion control configurations is determined based on a difference between associated sequential imaging positions.

12. The apparatus of claim 1, wherein the processor is further configured to determine the motion control configuration, and wherein the processor configured to control, with an output of a motion control configuration, the ultrasound imaging probe to be physically repositioned further comprises transmit the motion control configuration to a robotic system that controls the ultrasound imaging probe based on the motion control configuration.

13. A method of medical ultrasound image data acquisition, comprising:
controlling, with an output of a motion control configuration, an ultrasound imaging probe to be physically repositioned from a first imaging position to a second imaging position;
controlling the ultrasound imaging probe to obtain an ultrasound image representative of a subject's body while the ultrasound imaging probe is positioned at the second imaging position;
retrieving a target imaging position for the ultrasound imaging probe from a memory;
determining a score based on a comparison between the second imaging position and the target imaging position;
generating a data tuple comprising the ultrasound image, the motion control configuration, and the score; and
storing the data tuple in the memory and train a predictive network for aligning the imaging probe to the target imaging position based on the data tuple.

14. The method of claim 13, wherein the motion control configuration includes one or more parameters for moving the ultrasound imaging probe to the second imaging position.

15. The method of claim 14, further comprising determining the one or more parameters.

16. The method of claim 14, wherein the ultrasound imaging probe is a transesophageal echocardiography (TEE) probe, and wherein the one or more parameters correspond to one or more of a movement of the ultrasound imaging probe along a left-right plane of the subject's body, a movement of the ultrasound imaging probe along an anterior-posterior plane of the subject's body, an orientation of an imaging plane of the ultrasound imaging probe, or a rotation of the ultrasound imaging probe with respect to an axis of the ultrasound imaging probe.

17. The method of claim 14, wherein the ultrasound imaging probe is a transthoracic echocardiography (TTE) probe, and wherein the one or more parameters correspond to at least one of a linear velocity or an angular velocity for moving the ultrasound imaging probe.

18. The method of claim 13, further comprising determine the motion control configuration, and wherein controlling, with an output of a motion control configuration, the ultrasound imaging probe to be physically repositioned further comprises transmitting the motion control configuration to a robotic system that controls the ultrasound imaging probe based on the motion control configuration.

19. The method of claim 13, further comprising:
   determine a plurality of motion control configurations;
   controlling, with an output of the plurality of motion control configurations, the ultrasound imaging probe to be physically repositioned to a plurality of imaging positions;
   controlling the ultrasound imaging probe to obtain a plurality of ultrasound images representative of a subject's body while the ultrasound imaging probe is positioned at the plurality of imaging positions;
   retrieving a target imaging position for the ultrasound imaging probe from the memory;
   determining a plurality of scores based on a comparison between the plurality of imaging positions and the target imaging position;
   generating a plurality of data tuples, each data tuple comprising one of each of the plurality of ultrasound images, the plurality of motion control configurations, and the plurality of scores; and
   storing the plurality of data tuples in the memory.

20. The method of claim 19, wherein the plurality of data tuples are stored in the memory as an ordered sequence, the ordering based on the sequence of imaging positions.

* * * * *